United States Patent
Rose et al.

(10) Patent No.: US 10,973,883 B2
(45) Date of Patent: Apr. 13, 2021

(54) REDUCED OXYGEN CARRIERS AND THEIR USE FOR THE TREATMENT OF CARBOXYHEMOGLOBINEMIA

(71) Applicant: University of Pittsburgh—Of the Commonwealth System of Higher Education, Pittsburgh, PA (US)

(72) Inventors: Jason Joseph Rose, Pittsburgh, PA (US); Qinzi Xu, Wexford, PA (US); Mark T. Gladwin, Pittsburgh, PA (US); Jesus Tejero Bravo, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/302,324

(22) PCT Filed: May 19, 2017

(86) PCT No.: PCT/US2017/033607
§ 371 (c)(1),
(2) Date: Nov. 16, 2018

(87) PCT Pub. No.: WO2017/201447
PCT Pub. Date: Nov. 23, 2017

(65) Prior Publication Data
US 2019/0290739 A1    Sep. 26, 2019

Related U.S. Application Data

(60) Provisional application No. 62/338,870, filed on May 19, 2016.

(51) Int. Cl.
| | |
|---|---|
| A61K 38/42 | (2006.01) |
| A61K 9/127 | (2006.01) |
| A61K 35/14 | (2015.01) |
| C01C 3/08 | (2006.01) |
| C07K 14/795 | (2006.01) |
| A61K 31/409 | (2006.01) |
| A61K 33/00 | (2006.01) |
| A61K 38/06 | (2006.01) |

(52) U.S. Cl.
CPC .............. *A61K 38/42* (2013.01); *A61K 9/127* (2013.01); *A61K 35/14* (2013.01); *C01C 3/08* (2013.01); *C07K 14/795* (2013.01); *A61K 31/409* (2013.01); *A61K 33/00* (2013.01); *A61K 38/063* (2013.01)

(58) Field of Classification Search
CPC .................................................. A61K 38/42
See application file for complete search history.

(56) References Cited

U.S. PATENT DOCUMENTS

| | | | |
|---|---|---|---|
| 4,761,209 A | 8/1988 | Bonaventura et al. | |
| 5,900,402 A | 5/1999 | Shorr | |
| 5,985,332 A | 11/1999 | Barnikol et al. | |
| 10,421,800 B2* | 9/2019 | Gladwin | C07K 14/795 |
| 2004/0258745 A1 | 12/2004 | Kai et al. | |
| 2006/0003923 A1 | 1/2006 | Tsuchida et al. | |
| 2009/0117207 A1 | 5/2009 | Zoltani et al. | |
| 2011/0312914 A1 | 12/2011 | Kano et al. | |
| 2012/0220529 A1* | 8/2012 | Tye | A61K 38/42 |
| | | | 514/13.4 |
| 2015/0031599 A1* | 1/2015 | Abuchowski | A61K 47/60 |
| | | | 514/1.5 |
| 2016/0039910 A1 | 2/2016 | Gladwin et al. | |

FOREIGN PATENT DOCUMENTS

| | | | | |
|---|---|---|---|---|
| JP | 5619500 | 11/2014 | | |
| WO | WO 2014/150413 | * 9/2014 | ............. | A61K 38/41 |
| WO | WO 2015/179344 | 11/2015 | | |

OTHER PUBLICATIONS

Burmester et al., "A Vertebrate Globin Expressed in the Brain," *Nature*, vol. 407:520-523, 2000.
Dewilde et al., "Biochemical Characterization and Ligand Binding Properties of Neuroglobin, a Novel Member of the Globin Family," *J. Biol. Chem.*, vol. 276:38949-38955, 2001.
Henkel-Hanke et al., "Artificial Oxygen Carriers: A Current Review," *AANA J.*, vol. 75:205-211, 2007.
Huang et al., "Enzymatic Function of Hemoglobin as a Nitrite Reductase that Produces NO Under Allosteric Control," *J. Clin. Invest.*, vol. 115:2099-2107, 2005.
Rose et al., "Developing an Antidotal Therapy for Carbon Monoxide Poisoning that Reverses Hemodynamic Collapse, Mitochondrial Dysfunction and Death," Poster Presentation at the Pittsburgh International Lung Conference, Munich, Germany, Oct. 1, 2015.
Rose et al., "Recombinant Neuroglobin as a Novel Antidote for CO Poisoning that Restores Mitochondrial Respiration," Abstract and Poster Presentation at the American Thoracic Society International Conference, San Francisco, California, May 20, 2015.
Tiso et al., "Human Neuroglobin Functions as a Redox-regulated Nitrite Reductase," *J. Biol. Chem.*, vol. 286:18277-18289, 2011.
Unzai et al., "Rate Constants for $O_2$ and CO Binding to the $\alpha$ and $\beta$ Subunits within the R and T States of Human Hemoglobin," *J. Biol. Chem.*, vol. 273:23150-23159, 1998.

* cited by examiner

*Primary Examiner* — Amber D Steele
(74) *Attorney, Agent, or Firm* — Klarquist Sparkman, LLP

(57) ABSTRACT

In vitro and in vivo methods of removing carbon monoxide from hemoglobin in blood or animal tissue are described. Methods of treating carboxyhemoglobinemia (carbon monoxide poisoning) in a subject are also described. The methods include administering natural or artificial oxygen carriers that are in their reduced form. Methods of producing a reduced oxygen carrier are further described. Methods of treating cyanide poisoning or hydrogen sulfide poisoning with oxygen carriers are also described.

13 Claims, 12 Drawing Sheets

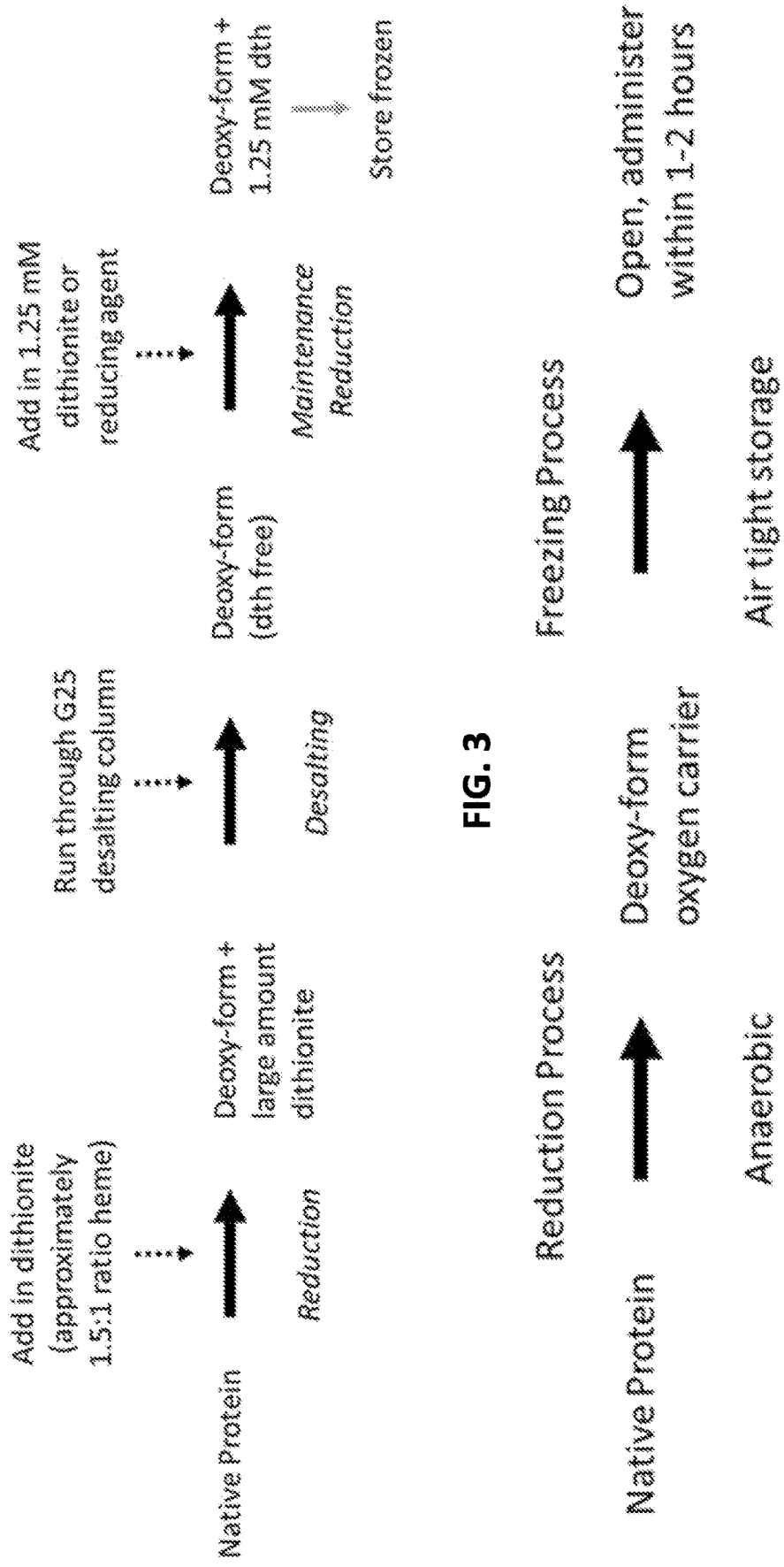

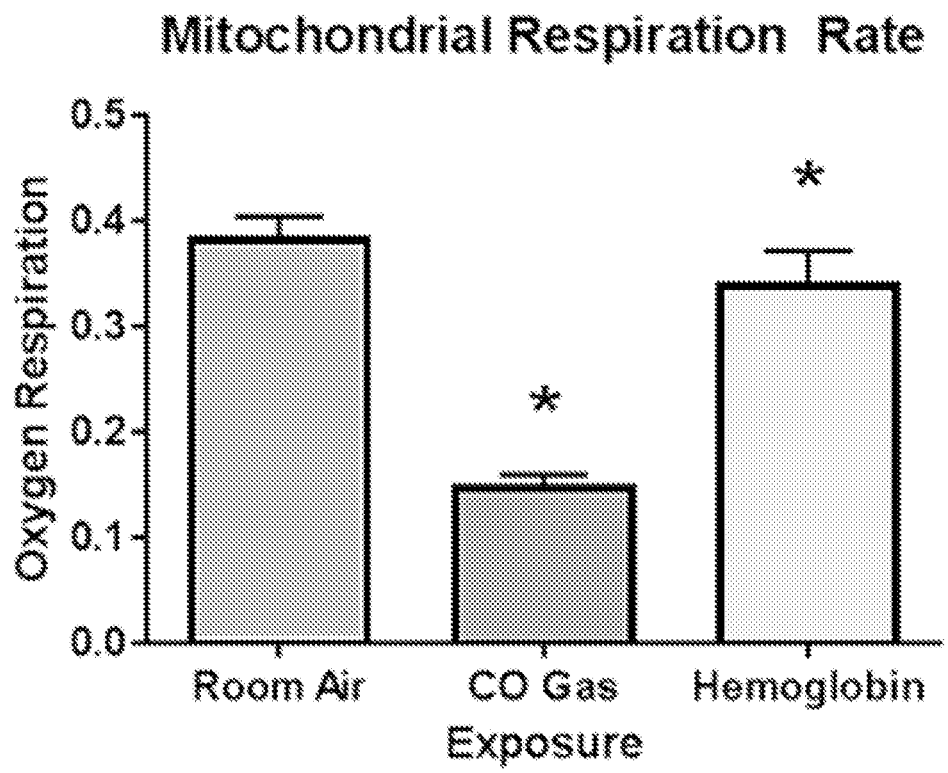
FIG. 12
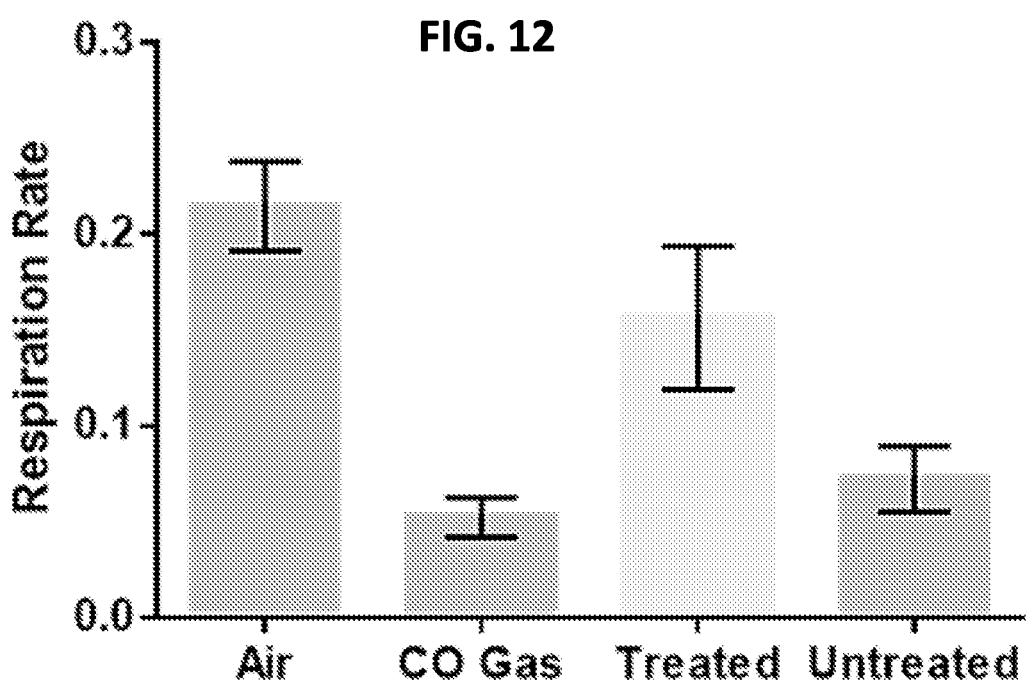

REDUCED OXYGEN CARRIERS AND THEIR USE FOR THE TREATMENT OF CARBOXYHEMOGLOBINEMIA

CROSS REFERENCE TO RELATED APPLICATIONS

This application is the U.S. National Stage of International Application No. PCT/US2017/033607, filed May 19, 2017, published in English under PCT Article 21(2), which claims the benefit of U.S. Provisional Application No. 62/338,870, filed May 19, 2016, which is herein incorporated by reference in its entirety.

ACKNOWLEDGMENT OF GOVERNMENT SUPPORT

This invention was made with government support under grant numbers HL125886, HL110849, HL007563 and HL103455, awarded by the National Institutes of Health. The government has certain rights in the invention.

FIELD

This disclosure concerns methods of treating carboxyhemoglobinemia using natural or artificial oxygen carriers in their reduced form. This disclosure further concerns a process for producing reduced globin proteins for use as oxygen carriers. Also described are methods of treating cyanide poisoning and hydrogen sulfide poisoning using oxygen carriers.

BACKGROUND

Inhalation exposure to carbon monoxide represents a major cause of environmental poisoning. Individuals can be exposed to carbon monoxide in the air under a variety of different circumstances, such as house fires, generators or outdoor barbeque grills used indoors, or during suicide attempts in closed spaces. Carbon monoxide binds to hemoglobin and to hemoproteins in cells, in particular the enzymes of the respiratory transport chain. The accumulation of carbon monoxide bound to hemoglobin and other hemoproteins impairs oxygen delivery and oxygen utilization for oxidative phosphorylation. This ultimately results in severe hypoxic and ischemic injury to vital organs such as the brain and the heart. Individuals who accumulate greater than 10% carbon carboxyhemoglobin in their blood are at risk for brain injury and neurocognitive dysfunction. Patients with very high carboxyhemoglobin levels typically suffer from irreversible brain injury, respiratory failure and/or cardiovascular collapse.

Despite the availability of methods to rapidly diagnose carbon monoxide poisoning with standard arterial and venous blood gas analysis and co-oximetry, and despite an awareness of risk factors for carbon monoxide poisoning, there are currently no available antidotes for this toxic exposure. The current therapy is to give 100% oxygen by face mask, and when possible to expose patients to hyperbaric oxygen. The mechanism behind hyperbaric oxygen therapy is the oxygen will increase the rate of release of the carbon monoxide from hemoglobin and from tissues and accelerate the natural clearance of carbon monoxide. However, this therapy has only a modest effect on carbon monoxide clearance rates, and based on the complexity of hyperbaric oxygen facilities, this therapy is not available in the field and is often associated with significant treatment delays and transportation costs.

SUMMARY

A need exists for effective, rapid and readily available therapies to treat carboxyhemoglobinemia (also known as carbon monoxide poisoning), cyanide poisoning and hydrogen sulfide poisoning.

Provided herein is a method of treating carboxyhemoglobinemia in a subject that includes selecting a subject with carboxyhemoglobinemia; and administering to the subject a therapeutically effective amount of a composition that includes a natural or artificial oxygen carrier, wherein the oxygen carrier is in its reduced form. In some embodiments, the composition further includes a reducing agent, such as a mild reducing agent at a non-toxic concentration.

Also provided are methods of removing carbon monoxide from hemoglobin in blood or animal tissue. The methods include contacting the blood or animal tissue with a composition that includes a natural or artificial oxygen carrier, wherein the oxygen carrier is in its reduced form. In some embodiments, the method is an in vitro method. In other embodiments, the method is an in vivo method.

Further provided is a method of preparing a reduced oxygen carrier. In some embodiments, the method includes contacting the oxygen carrier with a first reducing agent to produce an oxygen carrier-reducing agent composition; and passing the oxygen carrier-reducing agent composition over a desalting column to form a reduced oxygen carrier composition. The preparation of the reduced oxygen carrier is performed in an anaerobic environment.

Also provided is a method of treating cyanide poisoning in a subject by selecting a subject with cyanide poisoning and administering to the subject a therapeutically effective amount of a composition that includes a natural or an artificial oxygen carrier, wherein the oxygen carrier is in its oxidized form.

Further provided is a method of treating hydrogen sulfide ($H_2S$) poisoning by selecting a subject with $H_2S$ poisoning and administering to the subject a therapeutically effective amount of a composition that includes a natural or an artificial oxygen carrier, wherein the oxygen carrier is in its reduced form.

The foregoing and other objects, features, and advantages of the invention will become more apparent from the following detailed description, which proceeds with reference to the accompanying figures.

BRIEF DESCRIPTION OF THE DRAWINGS

FIG. 2 is a flow diagram of the steps of a method disclosed herein for the preparation of reduced oxygen carriers.

FIG. 3 is a flow diagram of a method for using oxygen carriers and artificial oxygen carriers to treat carbon monoxide poisoning.

(FIG. 4A) Carboxylated RBCs mixed with PBS. (FIG. 4B and FIG. 4C) Two sample experiments where different amounts of carboxylated RBCs were mixed with Mb. Black and red points indicate the concentration of carboxylated Hb and Mb, respectively.

(FIG. 10A) CO inhibits respiration of isolated liver mitochondria, persistent over 3 reoxygenations (CO1, CO2, CO3) compared to pre-CO exposure (Air). (FIG. 10B) CO inhibits heart respiration over 3 reoxygenations (CO, CO2, CO3) compared to pre-CO exposure (Air).

FIG. 11 is a graph showing that mitochondrial respiration is inhibited by CO, which is reversed with the addition of deoxy-hemoglobin. CO reduced respiration of isolated liver mitochondria by 60.5% (CO Gas) compared to pre-CO exposure (Room Air). The addition of 0.5 molar deoxy-hemoglobin increased respiration 95% (Hemoglobin) from the CO inhibited rate (CO Gas) (*=statistically significant).

FIG. 12 is a graph showing cardiac tissue respiration is inhibited by CO and reversed with the addition of deoxy-myoglobin. CO reduced respiration of LV homogenate by 75.6% (CO Gas) compared to pre-CO exposure (Air). The addition of 0.5 molar deoxy-myoglobin increased respiration 199% (Treated) from the CO inhibited rate (CO Gas). Without treatment, the rate of respiration remained as low as CO exposed respiration (CO Gas) even after reoxygenation (Untreated).

DETAILED DESCRIPTION

I. Abbreviations

Figure 1:
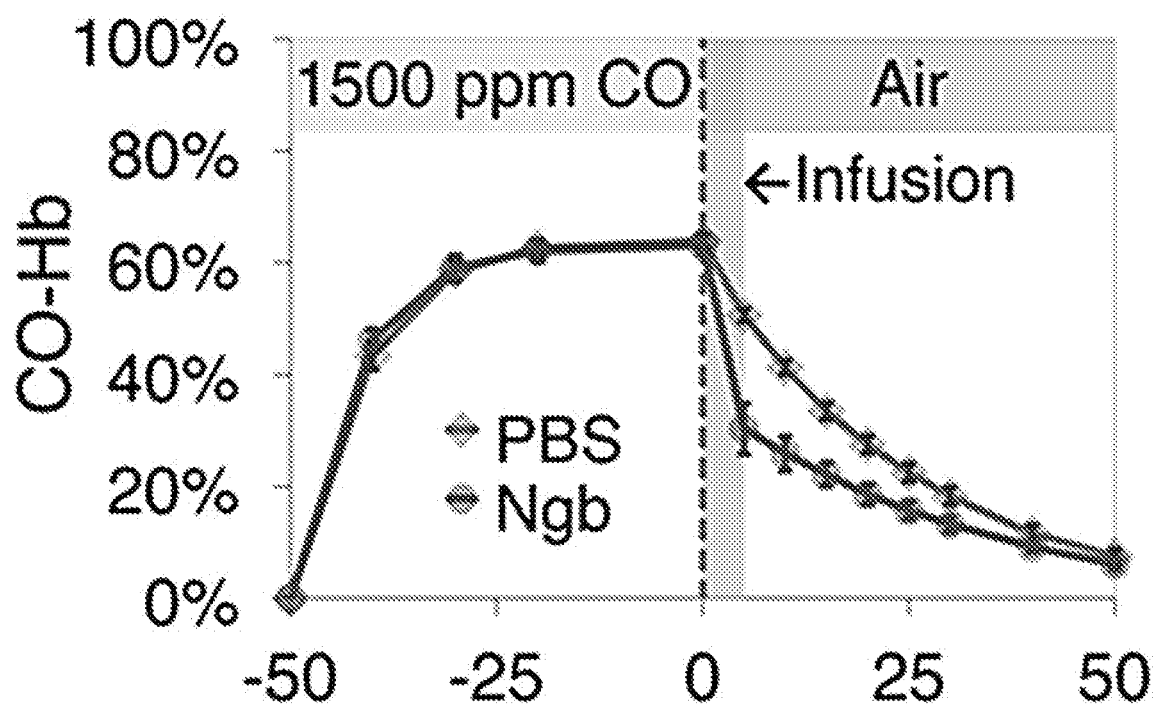
FIG. 1 is a graph showing the in vivo binding of CO from hemoglobin by recombinant neuroglobin in a mouse model for moderate CO poisoning.

CO carbon monoxide
CO-Hb carboxyhemoglobin
$H_2S$ hydrogen sulfide
Hb hemoglobin
HbCO carboxyhemoglobin
Hgb hemoglobin
IV intravenous
$LD_{50}$ lethal dose 50
LV left ventricle
Mb myoglobin
Mgb myoglobin
Ngb neuroglobin
PEG-Hb PEGylated hemoglobin
RBC red blood cell
rNgb recombinant neuroglobin
ROS reactive oxygen species II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent (e.g. an oxygen carrier), by any effective route. Exemplary routes of administration include, but are not limited to, injection or infusion (such as subcutaneous, intramuscular, intradermal, intraperitoneal, intrathecal, intravenous, intracerebroventricular, intrastriatal, intracranial and into the spinal cord), oral, intraductal, sublingual, rectal, transdermal, intranasal, vaginal and inhalation routes.

Antidote: An agent that neutralizes or counteracts the effects of a poison.

Carbon monoxide (CO): A colorless, odorless and tasteless gas that is toxic to human and animals when encountered at sufficiently high concentrations. CO is also produced during normal animal metabolism at low levels.

Carboxyhemoglobin (HbCO or CO-Hb): A stable complex of carbon monoxide (CO) and hemoglobin (Hb) that forms in red blood cells when CO is inhaled or produced during normal metabolism.

Carboxyhemoglobinemia or carbon monoxide poisoning: A condition resulting from the presence of excessive amounts of carbon monoxide in the blood. Typically, exposure to CO of 100 parts per million (ppm) or greater is sufficient to cause carboxyhemoglobinemia. Symptoms of mild acute CO poisoning include lightheadedness, confusion, headaches, vertigo, and flu-like effects; larger exposures can lead to significant toxicity of the central nervous system and heart, and even death. Following acute poisoning, long-term sequelae often occur. Carbon monoxide can also have severe effects on the fetus of a pregnant woman. Chronic exposure to low levels of carbon monoxide can lead to depression, confusion, and memory loss. Carbon monoxide mainly causes adverse effects in humans by combining with hemoglobin to form carboxyhemoglobin (HbCO) in the blood. This prevents oxygen binding to hemoglobin, reducing the oxygen-carrying capacity of the blood, leading to hypoxia. Additionally, myoglobin and mitochondrial cytochrome c oxidase are thought to be adversely affected. Carboxyhemoglobin can revert to hemoglobin, but the recovery takes time because the HbCO complex is fairly stable. Current methods of treatment for CO poisoning including administering 100% oxygen or providing hyperbaric oxygen therapy.

Contacting: Placement in direct physical association; includes both in solid and liquid form. When used in the context of an in vivo method, "contacting" also includes administering.

Cyanide poisoning: A type of poisoning that results from exposure to some forms of cyanide, such as hydrogen cyanide gas and cyanide salt. Cyanide poisoning can occur from inhaling smoke from a house fire, exposure to metal polishing, particular insecticides and certain seeds (such as apple seeds). Early symptoms of cyanide poisoning include headache, dizziness, rapid heart rate, shortness of breath and vomiting. Later symptoms include seizures, slow heart rate, low blood pressure, loss of consciousness and cardiac arrest.

Cytoglobin: A globin molecule that is ubiquitously expressed in all tissues. Cytoglobin is a hexacoordinate hemoglobin that has been reported to facilitate diffusion of oxygen through tissues, reduce nitrite to nitric oxide, and play a cytoprotective role in hypoxic conditions and under oxidative stress.

Globin: A heme-containing protein involved in the binding and/or transport of oxygen. Globins include, for example, hemoglobin, myoglobin, neuroglobin and cytoglobin.

Hemocyanin: A type of protein that transports oxygen throughout the body of some invertebrate animals. Hemocyanins are metalloproteins that contain two copper atoms that reversibly bind a single oxygen molecule. Hemocyanins are found only in the phylum Mollusca and the phylum Arthropoda.

Hemoglobin (Hb): The iron-containing oxygen-transport metalloprotein in the red blood cells of the blood in vertebrates and other animals. In humans, the hemoglobin molecule is an assembly of four globular protein subunits. Each subunit is composed of a protein chain tightly associated with a non-protein heme group. Each protein chain arranges into a set of alpha-helix structural segments connected together in a globin fold arrangement, so called because this arrangement is the same folding motif used in other heme/globin proteins. This folding pattern contains a pocket which strongly binds the heme group.

Hemoglobin-based oxygen carrier (HBOC): A transfusable fluid of purified, recombinant and/or modified hemoglobin that functions as an oxygen carrier. A number of HBOCs are known and/or in clinical development. Examples of HBOCs include, but are not limited to, DCLHb (HEMASSIST™; Baxter), MP4 (HEMOSPAN™; Sangart), pyridoxylated Hb POE-conjugate (PHP)+catalase & SOD (Apex Biosciences), O—R-PolyHbA$_0$ (HEMOLINK™; Hemosol), PolyBvHb (HEMOPURE™; Biopure), PolyHb (POLYHEME™; Northfield), rHb1.1 (OPTRO™; Somatogen), PEG-Hemoglobin (Enzon), OXYVITA™ and HBOC-201 (Greenburg and Kim, *Crit Care* 8 (Suppl 2):S61-S64, 2004; to Lintel Hekkert et al., *Am J Physiol Heart Circ Physiol* 298:H1103-H1113, 2010; Eisenach, *Anesthesiology* 111:946-963, 2009).

Heterologous: A heterologous protein or polypeptide refers to a protein or polypeptide derived from a different source or species.

Hydrogen sulfide poisoning: A type of poisoning resulting from excess exposure to hydrogen sulfide ($H_2S$). $H_2S$ binds iron in the mitochondrial cytochrome enzymes and prevents cellular respiration. Exposure to lower concentrations of $H_2S$ can cause eye irritation, sore throat, coughing, nausea, shortness of breath, pulmonary edema, fatigue, loss of appetite, headaches, irritability, poor memory and dizziness. Higher levels of exposure can cause immediate collapse, inability to breath and death.

Isolated: An "isolated" biological component (such as a nucleic acid molecule, protein, or cell) has been substantially separated or purified away from other biological components in the cell, blood or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Methemoglobin: The oxidized form of hemoglobin in which the iron in the heme component has been oxidized from the ferrous (+2) to the ferric (+3) state. This renders the hemoglobin molecule incapable of effectively transporting and releasing oxygen to the tissues. Normally, there is about 1% of total hemoglobin in the methemoglobin form.

Myoglobin (Mb): A member of the globin family of proteins. Myoglobin is an iron- and oxygen-binding protein found in the muscle tissue of all vertebrates and nearly all mammals. In humans, myoglobin is only found in the bloodstream after muscle injury. Unlike hemoglobin, myoglobin contains only one binding site for oxygen (on the one heme group of the protein), but its affinity for oxygen is greater than the affinity of hemoglobin for oxygen.

Neuroglobin (Ngb): A member of the globin family of proteins. The physiological function of neuroglobin is currently unknown, but is thought to provide protection under hypoxic or ischemic conditions. Neuroglobin is expressed in the central and peripheral nervous system, cerebral spinal fluid, retina and endocrine tissues.

Oxidizing agent: A substance that is capable of accepting an electron from another substance (also referred to as "oxidizing" a substance). An oxidizing agent gains electrons and is reduced in a chemical reaction. An oxidizing agent is also known as an "electron acceptor."

Oxygen carrier: Molecules or compounds that are capable of binding, transporting and releasing oxygen in the body. Oxygen carriers include natural proteins, such as hemoglobin, myoglobin and hemocyanin, as well as artificial oxygen carriers, including hemoglobin-based oxygen carriers (HBOCs), perfluorocarbons (PFCs), liposome-encapsulated hemoglobin and porphyrin metal complexes.

Peptide or Polypeptide: A polymer in which the monomers are amino acid residues which are joined together through amide bonds. When the amino acids are alpha-amino acids, either the L-optical isomer or the D-optical isomer can be used, the L-isomers being preferred. The terms "peptide," "polypeptide" or "protein" as used herein are intended to encompass any amino acid sequence and include modified sequences, including modified globin proteins. The terms "peptide" and "polypeptide" are specifically intended to cover naturally occurring proteins, as well as those which are recombinantly or synthetically produced.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
| --- | --- |
| Ala | Ser |
| Arg | Lys |

-continued

| Original Residue | Conservative Substitutions |
| --- | --- |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, serine or threonine, is substituted for (or by) a hydrophobic residue, for example, leucine, isoleucine, phenylalanine, valine or alanine; (b) a cysteine or proline is substituted for (or by) any other residue; (c) a residue having an electropositive side chain, for example, lysine, arginine, or histidine, is substituted for (or by) an electronegative residue, for example, glutamine or aspartic acid; or (d) a residue having a bulky side chain, for example, phenylalanine, is substituted for (or by) one not having a side chain, for example, glycine.

Pharmaceutically acceptable carriers: The pharmaceutically acceptable carriers of use are conventional. Remington's Pharmaceutical Sciences, by E. W. Martin, Mack Publishing Co., Easton, Pa., 15th Edition, 1975, describes compositions and formulations suitable for pharmaceutical delivery of the compositions disclosed herein.

In general, the nature of the carrier will depend on the particular mode of administration being employed. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Porphyrin: An organic compound containing four pyrrole rings, functioning as a metal-binding cofactor in hemoglobin, chlorophyll and certain enzymes.

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. The term recombinant includes nucleic acids and proteins that have been altered by addition, substitution, or deletion of a portion of a natural nucleic acid molecule or protein.

Reducing agent: An element or compound that loses (or "donates") an electron to another chemical species in a redox chemical reaction. A reducing agent is typically in one of its lower possible oxidation states, and is known as the electron donor. A reducing agent is oxidized, because it loses electrons in the redox reaction. Exemplary reducing agents include, but are not limited to, sodium dithionite, ascorbic acid, N-acetylcysteine, methylene blue, glutathione, cytochrome b5/b5-reductase, hydralazine, earth metals, formic acid and sulfite compounds.

Sequence identity/similarity: The identity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and C. elegans sequences).

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Subject: Living multi-cellular organisms, including vertebrate organisms, a category that includes both human and non-human mammals.

Synthetic: Produced by artificial means in a laboratory, for example a synthetic polypeptide can be chemically synthesized in a laboratory.

Therapeutically effective amount: A quantity of compound or composition, for instance, an oxygen carrier, sufficient to achieve a desired effect in a subject being treated. For instance, this can be the amount necessary to scavenge carbon monoxide in the blood or tissues, reduce the level of HbCO in the blood, and/or reduce one or more signs or symptoms associated with carbon monoxide poisoning.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Oxygen carriers include both natural oxygen carriers and artificial oxygen carriers. Examples of natural oxygen carriers include hemoglobin, such as hemoglobin from humans, bovines or other living organisms; concentrated red blood cells or myoglobin from humans, bovines, or other living organisms; and hemocyanin originating from, for example, Arthropoda or other living organisms. Examples of artificial oxygen carriers include highly functional oxygen carriers derived from natural oxygen carriers, such as modified hemoglobin and liposome-encapsulated hemoglobin; completely-synthesized oxygen carriers, such as compounds in which porphyrin metallic complexes are incorporated in albumin, albumin dimers, and albumin polymers, and perfluorocarbons; and recombinant oxygen carriers, such as recombinant/modified hemoglobin. These oxygen carriers can replace red blood cells of humans and other animals.

These oxygen carriers are used to supply oxygen to an ischemic site or tumor tissue, for blood transfusion to a patient, such as a patient with massive bleeding, to provide an organ-preserving perfusion fluid, or as an extracorporeal circulation fluid (U.S. Publication Nos. 2004/0258745 and 2006/0003923). An example of the porphyrin metal complex is a 2-[8-(2methyl-1-imidazolyl)octanoyloxymethyl]-5,10,15,20-tetrakis[α,α,α,α,-o-(1-methylcyclohexanoylamino) phenyl]porphinato complex (U.S. Patent Application Publication No. 2006/0003923).

A liposome-encapsulated hemoglobin includes a hemoglobin encapsulated in an inner layer of a liposome formed of a lipid bilayer, and various preparation methods and investigations thereof have been described (U.S. Patent Application Publication No. 2004/0258745).

Myoglobin and hemoglobin are five-coordinated heme proteins that only have one histidine permanently bound to the heme. Myoglobin has an affinity for CO 60 times that of $O_2$. (Nelson et al., "Carbon Monoxide" in Goldfrank's Toxicologic Emergencies (9th ed.), New York: McGraw-Hill. pp. 1658-1670, 2011.) The reaction of the iron atom from a heme group is depicted as follows:

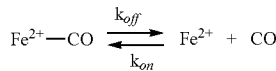

where $k_{on}$ and $k_{off}$ are the rates of CO binding and dissociation, respectively.

TABLE 1

Binding and dissociation constants for myoglobin and hemoglobin

| | $k_{on}$ $(M^{-1}s^{-1})$ | $k_{off}$ $(s^{-1})$ | $K_d$ (M) |
|---|---|---|---|
| Equine Myoglobin | $0.51 \times 10^6$ | 0.035 | $6.88 \times 10^{-8}$ |
| Cytochrome c oxidase | $7 \times 10^4$ | 0.023 | $3.29 \times 10^{-7}$ |

TABLE 1-continued

Binding and dissociation constants for myoglobin and hemoglobin

| | $k_{on}$ $(M^{-1}s^{-1})$ | $k_{off}$ $(s^{-1})$ | $K_d$ (M) |
|---|---|---|---|
| Human Hb (alpha subunit, R-state) | $6 \times 10^6$ | 0.012 | $2.00 \times 10^{-9}$ |
| Human Hb (alpha subunit, T-state) | $0.12 \times 10^6$ | 0.21 | $1.75 \times 10^{-6}$ |
| Human Hb (beta subunit, R-state) | $7.4 \times 10^6$ | 0.007 | $9.46 \times 10^{-10}$ |
| Human Hb (beta subunit, T-state) | $0.05 \times 10^6$ | 0.19 | $3.80 \times 10^{-6}$ |

Myoglobin data from Wan et al. (*Proc Natl Acad Sci USA* 95(22): 12825-12831, 1998)
Cytochrome c data from Cooper et al. (*J. Cereb Blood Flow Metab* 19(1): 27-38, 1999
Hemoglobin data from PCT Publication No. WO 2014/150413

Myoglobin has a 60-fold higher affinity for CO than oxygen and thus preferentially binds to CO in tissue. Non-CO bound Hb can act as an additional target for CO, as reduced Hb in the presence of CO acts as a reservoir for CO binding. Modified hemoglobin or myoglobin (artificial oxygen carriers) act in a similar manner as naturally occurring compounds. Additionally, these agents can be given already bound with oxygen, increasing oxygen delivery to tissue while binding up CO.

IV. Methods of Treating Carboxyhemoglobinemia

Provided herein are methods of treating carboxyhemoglobinemia in a subject. The methods include selecting a subject with carboxyhemoglobinemia, and administering to the subject a therapeutically effective amount of a composition that includes a natural oxygen carrier or an artificial oxygen carrier in its reduced form.

It is not necessary for 100% of the natural or artificial oxygen carrier included in the composition to be reduced in order for the oxygen carrier to be considered in reduced form. In some embodiments, at least 70% of the oxygen carrier is reduced, such as at least 75%, at least 80%, at least 85%, at least 90%, at least 95%, at least 96%, at least 97%, at least 98% or at least 99%. In particular embodiments, 75-100%, 80-100%, 85-100%, 90-100% or 95-100% of the oxygen carrier is reduced.

In some embodiments, the composition further includes a reducing agent. The reducing agent can be any reducing agent that can be safely administered to a subject, such as a human subject (for example, an agent with minimal and/or tolerable toxicity). In some examples, the reducing agent includes sodium dithionite, ascorbic acid, N-acetylcysteine, methylene blue, glutathione, cytochrome b5/b5-reductase, hydralazine, or any combination thereof. In some embodiments, the method further includes adding a second reducing agent to the reduced oxygen carrier composition. In most cases, the second reducing agent is added to the composition at a concentration that is the lowest effective concentration (for maintaining the oxygen carrier in its reduced form) that is safely tolerated physiologically, such as by a human. In some examples, the concentration of reducing agent in the composition is about 10 μM to about 100 mM, such as about 50 μM to about 50 mM, about 100 μM to about 25 mM, about 250 μM to about 10 mM, about 500 μM to about 5 mM or about 750 μM to about to about 1 mM. In particular examples, the concentration of the reducing agent in the composition is no more than about 1.0 mM, no more than about 1.5 mM, no more than about 2.0 mM or no more than about 2.5 mM.

In some embodiments, the natural oxygen carrier includes a globin protein. In some examples, the globin protein includes hemoglobin. In other examples, the globin protein includes myoglobin. In yet other examples, the globin protein includes neuroglobin or cytoglobin. In particular non-limiting examples, the globin protein is a human globin protein, such as human hemoglobin, human myoglobin, human neuroglobin or human cytoglobin. In other non-limiting examples, the globin protein is from a non-human animal, such as a bovine globin protein or an equine globin protein.

In some embodiments, the natural oxygen carrier includes a hemocyanin, such as mollusk hemocyanin or arthropod hemocyanin.

In some embodiments, the artificial oxygen carrier includes a hemoglobin-based oxygen carrier (HBOC). A number of HBOCs are known in the art. An appropriate HBOC can be selected and reduced for use in the disclosed methods. In some examples, the HBOC is DCLHb (HEMASSIST™; Baxter), MP4 (HEMOSPAN™; Sangart), pyridoxylated Hb POE-conjugate (PHP) (Apex Biosciences), O—R-PolyHb$A_0$ (HEMOLINK™; Hemosol), PolyBvHb (HEMOPURE™; Biopure), PolyHb (POLYHEME™; Northfield), rHb1.1 (OPTRO™; Somatogen), PEG-Hemoglobin (Enzon), OXYVITA™ and HBOC-201 (Greenburg and Kim, *Crit Care* 8 (Suppl 2):S61-S64, 2004; to Lintel Hekkert et al., *Am J Physiol Heart Circ Physiol* 298:H1103-H1113, 2010; Eisenach, *Anesthesiology* 111: 946-963, 2009).

In some embodiments, the artificial oxygen carrier includes a liposome-encapsulated globin protein, such as a liposome-encapsulated hemoglobin or a liposome-encapsulated myoglobin. In other embodiments, the artificial oxygen carrier is a modified globin protein, such as a modified hemoglobin, modified myoglobin, modified neuroglobin or modified cytoglobin.

In some embodiments, the artificial oxygen carrier includes a porphyrin metal complex. For example, the artificial oxygen carrier may include a porphyrin metallic complex derivative solubilized by the addition of a carrier protein (for example, albumin, ceruloplasmin, hemopexin) or an organic compound (for example, a perfluorocarbon).

Also provided herein are methods of removing carbon monoxide from hemoglobin in blood or animal tissue. The methods include contacting the blood or animal tissue with a composition that includes a natural oxygen carrier or an artificial oxygen carrier in its reduced form.

In some embodiments, the method is an in vivo method, where contacting the blood or animal tissue with a composition comprising a natural or an artificial oxygen carrier includes administering a therapeutically effective amount of the composition to a subject. In some examples, the method further includes selecting a subject with carboxyhemoglobinemia prior to administering the composition comprising the natural or artificial oxygen carrier to the subject. In some examples, the selected subject with carboxyhemoglobinemia has at least 5%, at least 10%, at least 15%, at least 20%, at least 30%, at least 40% or at least 50% carboxyhemoglobin in their blood.

In other embodiments, the method of removing carbon monoxide from hemoglobin in blood or animal tissue is an in vitro method.

In some embodiments of the method for removing carbon monoxide from hemoglobin in blood or animal tissue, the composition further includes a reducing agent. The reducing agent can be any reducing agent that can be safely administered to a subject, such as a human subject (for example, an agent with minimal and/or tolerable toxicity). In some examples, the reducing agent includes sodium dithionite, ascorbic acid, N-acetylcysteine, methylene blue, glutathione, cytochrome b5/b5-reductase, hydralazine, or any combination thereof.

In some embodiments of the method for removing carbon monoxide from hemoglobin in blood or animal tissue, the natural oxygen carrier includes a globin protein. In some examples, the globin protein includes hemoglobin. In other examples, the globin protein includes myoglobin. In yet other examples, the globin protein includes neuroglobin or cytoglobin. In particular non-limiting examples, the globin protein is a human globin protein, such as human hemoglobin, human myoglobin, human neuroglobin or human cytoglobin. In other non-limiting examples, the globin protein is from a non-human animal, such as a bovine globin protein or an equine globin protein.

In some embodiments of the method for removing carbon monoxide from hemoglobin in blood or animal tissue, the natural oxygen carrier includes a hemocyanin, such as mollusk hemocyanin or arthropod hemocyanin.

In some embodiments of the method for removing carbon monoxide from hemoglobin in blood or animal tissue, the artificial oxygen carrier includes a hemoglobin-based oxygen carrier (HBOC). A number of HBOCs are known in the art. An appropriate HBOC can be selected and reduced for use in the disclosed methods. In some examples, the HBOC is DCLHb (HEMASSIST™; Baxter), MP4 (HEMOSPAN™; Sangart), pyridoxylated Hb POE-conjugate (PHP) (Apex Biosciences), O—R—PolyHb$A_0$ (HEMOLINK™; Hemosol), PolyBvHb (HEMOPURE™; Biopure), PolyHb (POLYHEME™; Northfield), rHb1.1 (OPTRO™; Somatogen), PEG-Hemoglobin (Enzon), OXYVITA™ and HBOC-201 (Greenburg and Kim, *Crit Care* 8 (Suppl 2):S61-S64, 2004; to Lintel Hekkert et al., *Am J Physiol Heart Circ Physiol* 298:H1103-H1113, 2010; Eisenach, *Anesthesiology* 111:946-963, 2009).

In some embodiments of the method for removing carbon monoxide from hemoglobin in blood or animal tissue, the artificial oxygen carrier includes a liposome-encapsulated globin protein, such as a liposome-encapsulated hemoglobin or a liposome-encapsulated myoglobin. In other embodiments, the artificial oxygen carrier is a modified globin protein, such as a modified hemoglobin, modified myoglobin, modified neuroglobin or modified cytoglobin.

In some embodiments, the artificial oxygen carrier includes a porphyrin metal complex. For example, the artificial oxygen carrier may include a porphyrin metallic complex derivative solubilized by the addition of a carrier protein (for example, albumin, ceruloplasmin, hemopexin) or an organic compound (for example, a perfluorocarbon).

V. Methods of Treating Cyanide Poisoning

Cyanide is known to inhibit mitochondrial respiration, in a similar manner to CO-mediated inhibition of mitochondrial respiration by binding to the heme a3 center in cytochrome c oxidase. Although it partially binds the reduced form, cyanide binds strongest to the oxidized state of cytochrome c oxidase (complex IV of the electron transport chain) (Leavesley et al., *Toxicol Sci* 101(1):101-111, 2008). Similar to the ability of oxygen carriers to scavenge CO in the reduced state, oxygen carriers in the oxidized state, mediated through an oxidizing agent, are able to scavenge cyanide. Thus, the use of natural and artificial oxygen carriers for removing cyanide from cyano-hemoglobin located inside red blood cells, as well as other heme containing proteins in the body (such as cytochrome c oxidase), is contemplated herein.

Provided herein are methods of treating cyanide poisoning in a subject. In some embodiments, the method includes selecting a subject with cyanide poisoning; and administering to the subject a therapeutically effective amount of a composition comprising a natural or an artificial oxygen carrier, wherein the oxygen carrier is in its oxidized form.

It is not necessary for 100% of the natural or artificial oxygen carrier included in the composition to be oxidized in order for the oxygen carrier to be considered in oxidized form. In some embodiments, at least 70% of the oxygen carrier is oxidized, such as at least 75%, at least 80%, at least 85%, at least 90%, at least 95%, at least 96%, at least 97%, at least 98% or at least 99%. In particular embodiments, 75-100%, 80-100%, 85-100%, 90-100% or 95-100% of the oxygen carrier is oxidized.

In some embodiments, the composition further includes an oxidizing agent. The oxidizing agent can be any oxidizing agent that can be safely administered to a subject, such as a human subject (for example, an agent with minimal and/or tolerable toxicity). In some examples, the oxidizing agent includes an oxygen-containing gas mixture, an oxygen-containing liquid mixture, a ferricyanide salt (such as potassium ferricyanide), or any combination thereof. In some embodiments, the method further includes adding a second oxidizing agent to the oxidized oxygen carrier composition. In most cases, the second oxidizing agent is added to the composition at a concentration that is the lowest effective concentration (for maintaining the oxygen carrier in its oxidized form) that is safely tolerated physiologically, such as by a human. In some examples, the concentration of oxidizing agent in the composition is about 10 µM to about 100 mM, such as about 50 µM to about 50 mM, about 100 µM to about 25 mM, about 250 µM to about 10 mM, about 500 µM to about 5 mM or about 750 µM to about to about 1 mM. In particular examples, the concentration of the oxidizing agent in the composition is no more than about 1.0 mM, no more than about 1.5 mM, no more than about 2.0 mM or no more than about 2.5 mM.

In some embodiments, the natural oxygen carrier includes a globin protein. In some examples, the globin protein includes hemoglobin. In other examples, the globin protein includes myoglobin. In yet other examples, the globin protein includes neuroglobin or cytoglobin. In particular non-limiting examples, the globin protein is a human globin protein, such as human hemoglobin, human myoglobin, human neuroglobin or human cytoglobin. In other non-limiting examples, the globin protein is from a non-human animal, such as a bovine globin protein or an equine globin protein.

In some embodiments, the natural oxygen carrier includes a hemocyanin, such as mollusk hemocyanin or arthropod hemocyanin.

In some embodiments, the artificial oxygen carrier includes a hemoglobin-based oxygen carrier (HBOC). A number of HBOCs are known in the art. An appropriate HBOC can be selected and reduced for use in the disclosed methods. In some examples, the HBOC is DCLHb (HEMASSIST™; Baxter), MP4 (HEMOSPAN™; Sangart), pyridoxylated Hb POE-conjugate (PHP) (Apex Biosciences), O—R—PolyHbA$_0$ (HEMOLINK™; Hemosol), PolyBvHb (HEMOPURE™; Biopure), PolyHb (POLYHEME™; Northfield), rHb1.1 (OPTRO™; Somatogen), PEG-Hemoglobin (Enzon), OXYVITA™ and HBOC-201 (Greenburg and Kim, *Crit Care* 8 (Suppl 2):S61-S64, 2004; to Lintel Hekkert et al., *Am J Physiol Heart Circ Physiol* 298:H1103-H1113, 2010; Eisenach, *Anesthesiology* 111: 946-963, 2009).

In some embodiments, the artificial oxygen carrier includes a liposome-encapsulated globin protein, such as a liposome-encapsulated hemoglobin or a liposome-encapsulated myoglobin. In other embodiments, the artificial oxygen carrier is a modified globin protein, such as a modified hemoglobin, modified myoglobin, modified neuroglobin or modified cytoglobin.

In some embodiments, the artificial oxygen carrier includes a porphyrin metal complex. For example, the artificial oxygen carrier may include a porphyrin metallic complex derivative solubilized by the addition of a carrier protein (for example, albumin, ceruloplasmin, hemopexin) or an organic compound (for example, a perfluorocarbon).

Also provided herein are methods of removing cyanide from a heme-containing protein in blood or animal tissue. The methods include contacting the blood or animal tissue with a composition that includes a natural oxygen carrier or an artificial oxygen carrier in its oxidized form. In some embodiments, the heme-containing protein is hemoglobin or cytochrome c oxidase.

In some embodiments, the method is an in vivo method, where contacting the blood or animal tissue with a composition comprising a natural or an artificial oxygen carrier includes administering a therapeutically effective amount of the composition to a subject. In some examples, the method further includes selecting a subject with cyanide poisoning prior to administering the composition comprising the natural or artificial oxygen carrier to the subject.

In other embodiments, the method of removing cyanide from a heme-containing protein in blood or animal tissue is an in vitro method.

In some embodiments of the method for removing cyanide from a heme-containing protein in blood or animal tissue, the composition further includes an oxidizing agent. The oxidizing agent can be any oxidizing agent that can be safely administered to a subject, such as a human subject (for example, an agent with minimal and/or tolerable toxicity). In some examples, the oxidizing agent includes an oxygen-containing gas mixture, an oxygen-containing liquid mixture, a ferricyanide salt (such as potassium ferricyanide), or any combination thereof.

In some embodiments of the method for removing cyanide from a heme-containing protein in blood or animal tissue, the natural oxygen carrier includes a globin protein. In some examples, the globin protein includes hemoglobin. In other examples, the globin protein includes myoglobin. In yet other examples, the globin protein includes neuroglobin or cytoglobin. In particular non-limiting examples, the globin protein is a human globin protein, such as human hemoglobin, human myoglobin, human neuroglobin or human cytoglobin. In other non-limiting examples, the globin protein is from a non-human animal, such as a bovine globin protein or an equine globin protein.

In some embodiments of the method for removing cyanide from a heme-containing protein in blood or animal tissue, the natural oxygen carrier includes a hemocyanin, such as mollusk hemocyanin or arthropod hemocyanin.

In some embodiments of the method for removing cyanide from a heme-containing protein in blood or animal tissue, the artificial oxygen carrier includes a hemoglobin-based oxygen carrier (HBOC). A number of HBOCs are known in the art. An appropriate HBOC can be selected and reduced for use in the disclosed methods. In some examples, the HBOC is DCLHb (HEMASSIST™; Baxter), MP4 (HEMOSPAN™; Sangart), pyridoxylated Hb POE-conjugate (PHP) (Apex Biosciences), O—R—PolyHbA$_0$ (HEMOLINK™; Hemosol), PolyBvHb (HEMOPURE™; Biopure), PolyHb (POLYHEME™; Northfield), rHb1.1 (OPTRO™; Somatogen), PEG-Hemoglobin (Enzon), OXYVITA™ and HBOC-201 (Greenburg and Kim, *Crit Care* 8 (Suppl 2):S61-S64, 2004; to Lintel Hekkert et al., *Am J Physiol Heart Circ Physiol* 298:H1103-H1113, 2010; Eisenach, *Anesthesiology* 111:946-963, 2009).

In some embodiments of the method for removing cyanide from a heme-containing protein in blood or animal tissue, the artificial oxygen carrier includes a liposome-encapsulated globin protein, such as a liposome-encapsulated hemoglobin or a liposome-encapsulated myoglobin. In other embodiments, the artificial oxygen carrier is a modified globin protein, such as a modified hemoglobin, modified myoglobin, modified neuroglobin or modified cytoglobin. In some embodiments, the artificial oxygen carrier includes a porphyrin metal complex. For example, the artificial oxygen carrier may include a porphyrin metallic complex derivative solubilized by the addition of a carrier protein (for example, albumin, ceruloplasmin, hemopexin) or an organic compound (for example, a perfluorocarbon).

VI. Methods of Treating Hydrogen Sulfide (H$_2$S) Poisoning

Hydrogen sulfide is known to inhibit mitochondrial respiration, in a similar manner to CO-mediated inhibition of mitochondrial respiration. H$_2$S binds strongest to the reduced form of cytochrome c oxidase (complex IV of the electron transport chain) (Nicholls et al., *Biochem Soc Trans* 41(5):1312-1316, 2013). Similar to an oxygen carrier's ability to scavenge CO in the reduced state, oxygen carriers in the reduced state, mediated through a reducing agent, are able to scavenge H$_2$S. Thus, the use of natural and artificial oxygen carriers for removing H$_2$S from hemoglobin located inside red blood cells, as well as other heme containing proteins in the body (such as cytochrome c oxidase), is contemplated herein.

Provided herein are methods of treating hydrogen sulfide (H$_2$S) poisoning in a subject. In some embodiments, the method includes selecting a subject with H$_2$S poisoning; and administering to the subject a therapeutically effective amount of a composition comprising a natural or an artificial oxygen carrier, wherein the oxygen carrier is in its reduced form.

It is not necessary for 100% of the natural or artificial oxygen carrier included in the composition to be reduced in order for the oxygen carrier to be considered in reduced form. In some embodiments, at least 70% of the oxygen carrier is reduced, such as at least 75%, at least 80%, at least 85%, at least 90%, at least 95%, at least 96%, at least 97%, at least 98% or at least 99%. In particular embodiments, 75-100%, 80-100%, 85-100%, 90-100% or 95-100% of the oxygen carrier is reduced.

In some embodiments, the composition further includes a reducing agent. The reducing agent can be any reducing agent that can be safely administered to a subject, such as a human subject (for example, an agent with minimal and/or tolerable toxicity). In some examples, the reducing agent includes sodium dithionite, ascorbic acid, N-acetylcysteine, methylene blue, glutathione, cytochrome b5/b5-reductase, hydralazine, or any combination thereof. In some embodiments, the method further includes adding a second reducing agent to the reduced oxygen carrier composition. In most cases, the second reducing agent is added to the composition at a concentration that is the lowest effective concentration (for maintaining the oxygen carrier in its reduced form) that is safely tolerated physiologically, such as by a human. In some examples, the concentration of reducing agent in the composition is about 10 µM to about 100 mM, such as about 50 µM to about 50 mM, about 100 µM to about 25 mM, about 250 µM to about 10 mM, about 500 µM to about 5 mM or about 750 µM to about to about 1 mM. In particular examples, the concentration of the reducing agent in the composition is no more than about 1.0 mM, no more than about 1.5 mM, no more than about 2.0 mM or no more than about 2.5 mM.

In some embodiments, the natural oxygen carrier includes a globin protein. In some examples, the globin protein includes hemoglobin. In other examples, the globin protein includes myoglobin. In yet other examples, the globin protein includes neuroglobin or cytoglobin. In particular non-limiting examples, the globin protein is a human globin protein, such as human hemoglobin, human myoglobin, human neuroglobin or human cytoglobin. In other non-limiting examples, the globin protein is from a non-human animal, such as a bovine globin protein or an equine globin protein.

In some embodiments, the natural oxygen carrier includes a hemocyanin, such as mollusk hemocyanin or arthropod hemocyanin.

In some embodiments, the artificial oxygen carrier includes a hemoglobin-based oxygen carrier (HBOC). A number of HBOCs are known in the art. An appropriate HBOC can be selected and reduced for use in the disclosed methods. In some examples, the HBOC is DCLHb (HEMASSIST™; Baxter), MP4 (HEMOSPAN™; Sangart), pyridoxylated Hb POE-conjugate (PHP) (Apex Biosciences), O—R—PolyHbA$_0$ (HEMOLINK™; Hemosol), PolyBvHb (HEMOPURE™; Biopure), PolyHb (POLYHEME™; Northfield), rHb1.1 (OPTRO™; Somatogen), PEG-Hemoglobin (Enzon), OXYVITA™ and HBOC-201 (Greenburg and Kim, *Crit Care* 8 (Suppl 2):S61-S64, 2004; to Lintel Hekkert et al., *Am J Physiol Heart Circ Physiol* 298:H1103-H1113, 2010; Eisenach, *Anesthesiology* 111: 946-963, 2009).

In some embodiments, the artificial oxygen carrier includes a liposome-encapsulated globin protein, such as a liposome-encapsulated hemoglobin or a liposome-encapsulated myoglobin. In other embodiments, the artificial oxygen carrier is a modified globin protein, such as a modified hemoglobin, modified myoglobin, modified neuroglobin or modified cytoglobin.

In some embodiments, the artificial oxygen carrier includes a porphyrin metal complex. For example, the artificial oxygen carrier may include a porphyrin metallic complex derivative solubilized by the addition of a carrier protein (for example, albumin, ceruloplasmin, hemopexin) or an organic compound (for example, a perfluorocarbon).

Also provided herein are methods of removing H$_2$S from a heme-containing protein in blood or animal tissue. The methods include contacting the blood or animal tissue with a composition that includes a natural oxygen carrier or an artificial oxygen carrier in its reduced form. In some embodiments, the heme-containing protein is hemoglobin or cytochrome c oxidase.

In some embodiments, the method is an in vivo method, where contacting the blood or animal tissue with a composition comprising a natural or an artificial oxygen carrier includes administering a therapeutically effective amount of the composition to a subject. In some examples, the method further includes selecting a subject with H$_2$S poisoning prior to administering the composition comprising the natural or artificial oxygen carrier to the subject.

In other embodiments, the method of removing $H_2S$ from a heme-containing protein in blood or animal tissue is an in vitro method.

In some embodiments of the method for removing $H_2S$ from a heme-containing protein in blood or animal tissue, the composition further includes a reducing agent. The reducing agent can be any reducing agent that can be safely administered to a subject, such as a human subject (for example, an agent with minimal and/or tolerable toxicity). In some examples, the reducing agent includes sodium dithionite, ascorbic acid, N-acetylcysteine, methylene blue, glutathione, cytochrome b5/b5-reductase, hydralazine, or any combination thereof.

In some embodiments of the method for removing $H_2S$ from a heme-containing protein in blood or animal tissue, the natural oxygen carrier includes a globin protein. In some examples, the globin protein includes hemoglobin. In other examples, the globin protein includes myoglobin. In yet other examples, the globin protein includes neuroglobin or cytoglobin. In particular non-limiting examples, the globin protein is a human globin protein, such as human hemoglobin, human myoglobin, human neuroglobin or human cytoglobin. In other non-limiting examples, the globin protein is from a non-human animal, such as a bovine globin protein or an equine globin protein.

In some embodiments of the method for removing $H_2S$ from a heme-containing protein in blood or animal tissue, the natural oxygen carrier includes a hemocyanin, such as mollusk hemocyanin or arthropod hemocyanin.

In some embodiments of the method for removing $H_2S$ from a heme-containing protein in blood or animal tissue, the artificial oxygen carrier includes a hemoglobin-based oxygen carrier (HBOC). A number of HBOCs are known in the art. An appropriate HBOC can be selected and reduced for use in the disclosed methods. In some examples, the HBOC is DCLHb (HEMASSIST™; Baxter), MP4 (HEMOSPAN™; Sangart), pyridoxylated Hb POE-conjugate (PHP) (Apex Biosciences), O—R—PolyHbA$_0$ (HEMOLINK™; Hemosol), PolyBvHb (HEMOPURE™; Biopure), PolyHb (POLYHEME™; Northfield), rHb1.1 (OPTRO™; Somatogen), PEG-Hemoglobin (Enzon), OXYVITA™ and HBOC-201 (Greenburg and Kim, *Crit Care* 8 (Suppl 2):S61-S64, 2004; to Lintel Hekkert et al., *Am J Physiol Heart Circ Physiol* 298:H1103-H1113, 2010; Eisenach, *Anesthesiology* 111:946-963, 2009).

In some embodiments of the method for removing $H_2S$ from a heme-containing protein in blood or animal tissue, the artificial oxygen carrier includes a liposome-encapsulated globin protein, such as a liposome-encapsulated hemoglobin or a liposome-encapsulated myoglobin. In other embodiments, the artificial oxygen carrier is a modified globin protein, such as a modified hemoglobin, modified myoglobin, modified neuroglobin or modified cytoglobin.

In some embodiments, the artificial oxygen carrier includes a porphyrin metal complex. For example, the artificial oxygen carrier may include a porphyrin metallic complex derivative solubilized by the addition of a carrier protein (for example, albumin, ceruloplasmin, hemopexin) or an organic compound (for example, a perfluorocarbon).

VII. Methods of Preparing a Reduced Oxygen Carrier

Further provided herein is a method of preparing a reduced oxygen carrier. The method includes contacting the oxygen carrier with a first reducing agent to produce an oxygen carrier-reducing agent composition; and passing the oxygen carrier-reducing agent composition over a desalting column to form a reduced oxygen carrier composition. The preparation of the reduced oxygen carrier is performed in an anaerobic environment.

In some embodiments, the first reducing agent is contacted with the oxygen carrier at a ratio of 1:100 to 5:1 (reducing agent to oxygen carrier). In particular embodiments, the ratio of reducing agent to oxygen carrier is from 1:50 to 4:1, from 1:25 to 3:1, from 1:10 to 2:1, or from 1:5 to 1:1. In some examples, the ratio of reducing agent to oxygen carrier is about 5:1, about 4:1, about 3:1, about 2:1, about 1:1, about 1:2, about 1:5, about 1:10, about 1:20, about 1:30, about 1:40, about 1:50, about 1:60, about 1:70, about 1:80, about 1:90 or about 1:100.

In some embodiments, the method further includes adding a second reducing agent to the reduced oxygen carrier composition. In most cases, the second reducing agent is added at a concentration that is the lowest effective concentration (for maintaining the oxygen carrier in its reduced form) that is safely tolerated physiologically, such as by a human. In some examples, the second reducing agent is added at a concentration of about 10 µM to about 100 mM, such as about 50 µM to about 50 mM, about 100 µM to about 25 mM, about 250 µM to about 10 mM, about 500 µM to about 5 mM or about 750 µM to about to about 1 mM. In particular examples, the second reducing agent is added at a concentration of no more than about 1.0 mM, no more than about 1.5 mM, no more than about 2.0 mM or no more than about 2.5 mM.

The reducing agents can be any reducing agents that can be safely administered to a subject, such as a human or other mammalian subject (for example, an agent with minimal and/or tolerable toxicity). In some embodiments, the first reducing agent, the second reducing agent, or both, are selected from sodium dithionite, ascorbic acid, N-acetylcysteine, methylene blue, glutathione, hydralazine and cytochrome b5/b5-reductase, or any combination thereof.

In some embodiments, the method further includes freezing the reduced oxygen carrier composition to produce a frozen reduced oxygen carrier composition.

In some embodiments, the method further includes thawing the frozen reduced oxygen carrier composition.

In some embodiments, the method further includes administering the reduced oxygen carrier to a subject in need thereof, such as a subject that has carboxyhemoglobinemia (carbon monoxide poisoning) or hydrogen sulfide poisoning. In some examples, the subject has at least 5%, at least 10%, at least 15%, at least 20%, at least 30%, at least 40% or at least 50% carboxyhemoglobin in their blood.

VIII. Methods of Preparing an Oxidized Oxygen Carrier

Further provided herein is a method of preparing an oxidized oxygen carrier. The method includes contacting the oxygen carrier with a first oxidizing agent to produce an oxygen carrier-oxidizing agent composition; and passing the oxygen carrier-oxidizing agent composition over a desalting column to form an oxidized oxygen carrier composition. The preparation of the oxidized oxygen carrier is performed in an aerobic environment.

In some embodiments, the first oxidizing agent is contacted with the oxygen carrier at a ratio of 1:100 to 5:1 (oxidizing agent to oxygen carrier). In particular embodiments, the ratio of oxidizing agent to oxygen carrier is from 1:50 to 4:1, from 1:25 to 3:1, from 1:10 to 2:1, or from 1:5 to 1:1. In some examples, the ratio of oxidizing agent to oxygen carrier is about 5:1, about 4:1, about 3:1, about 2:1, about 1:1, about 1:2, about 1:5, about 1:10, about 1:20, about 1:30, about 1:40, about 1:50, about 1:60, about 1:70, about 1:80, about 1:90 or about 1:100.

In some embodiments, the first oxidizing agent is physically or chemically removed (example: ferricyanide) from the oxygen carrier through methods such as a desalting or gel chromatography.

In some embodiments, the method further includes adding a second oxidizing agent to the oxidized oxygen carrier composition. In most cases, the second oxidizing agent is added at a concentration that is the lowest effective concentration (for maintaining the oxygen carrier in its oxidized form) that is safely tolerated physiologically, such as by a human. In some examples, the second oxidizing agent is added at a concentration of about 10 µM to about 100 mM, such as about 50 µM to about 50 mM, about 100 µM to about 25 mM, about 250 µM to about 10 mM, about 500 µM to about 5 mM or about 750 µM to about to about 1 mM. In particular examples, the second oxidizing agent is added at a concentration of no more than about 1.0 mM, no more than about 1.5 mM, no more than about 2.0 mM or no more than about 2.5 mM.

The oxidizing agents can be any oxidizing agents that can be safely administered to a subject, such as a human or other mammalian subject (for example, an agent with minimal and/or tolerable toxicity). In some embodiments, the first oxidizing agent, the second oxidizing agent, or both, are selected from an oxygen-containing gas mixture, an oxygen-containing liquid mixture, a ferricyanide salt (such as potassium ferricyanide), or any combination thereof.

In some embodiments, the method further includes freezing the oxidized oxygen carrier composition to produce a frozen oxidized oxygen carrier composition.

In some embodiments, the method further includes thawing the frozen oxidized oxygen carrier composition.

In some embodiments, the method further includes administering the oxidized oxygen carrier to a subject in need thereof, such as a subject that has cyanide poisoning.

The following examples are provided to illustrate certain particular features and/or embodiments. These examples should not be construed to limit the disclosure to the particular features or embodiments described.

EXAMPLES

Example 1: Carbon Monoxide (CO) Scavenging Rapidly Removes Carboxyhemoglobin (HbCO) in CO Poisoned Mice In Vivo It was previously shown that exposure of mice to air with 1500 ppm CO gas for an average of 50 minutes caused HbCO levels to increase to 64%+/−1% (PCT Publication No. WO 2014/150413). Prior to exposure, mice were surgically instrumented with placement of femoral artery and vein catheters for blood pressure monitoring, blood sampling and infusions of either recombinant neuroglobin (rNgb), another type of CO scavenging globin protein, or PBS as a control. Mice were infused with 250 µL of 8-12 mM rNgb or PBS within 4 minutes using a Harvard infusion pump. Immediately after infusion and every 5 minutes, 5 µL of blood was collected for measurement of HbCO. As shown in FIG. 1, rNgb infusion rapidly reduced the HbCO level compared to PBS control. In particular, after 5 minutes of return to normal air, the HbCO levels dropped by an average of 32.8% in the group that received rNgb versus 13.3% in the group that received PBS (FIG. 1). After 60 minutes, the mice were sacrificed and the urinary bladder was found to contain millimolar concentrations of rNgb. This study demonstrated that rNgb acts as a CO chelator in vivo, quickly reducing HbCO levels, and is filtered through the kidneys.

Example 2: Materials and Methods

This example describes the methods and experimental procedures for the studies described in Examples 3-8.

Kinetics of Carboxylated RBCs Mixed with Myoglobin

Red blood cells were obtained by washing 50-100 µL of blood with PBS 5 to 7 times, and centrifugation at 1000×g for 5 to 10 minutes. The washed RBCs were diluted in 1 to 2 ml of PBS. RBCs were then deoxygenated on ice with slow stirring by a passing flow of argon gas for up to 1 hour. For anaerobic experiments, argon was passed briefly and an excess of sodium dithionite to Hb was added to the RBCs. Carboxylated red cell-encapsulated Hb was obtained by diluting the deoxygenated red blood cell solution with a ratio of at least 4:1. Excess CO was removed by washing the RBCs twice with degassed PBS (containing 5-10 mM dithionite for anaerobic experiments) and centrifugation for 5 minutes at 1000×g in degassed and septum-capped 15 mL centrifuge tubes. After washing, the RBCs were resuspended to a final concentration of 100-200 with an excess of sodium dithionite for anaerobic experiments.

Oxygenated or deoxygenated myoglobin (Mb) was prepared following the same procedure as that described for the experiments with pure Hb. In some experiments, after initiating the reaction, red cells were separated from Mb to measure absorbance spectra. In this case, the reaction temperature was regulated with an Isotemp stirring hotplate and water bath combination (Fisher Scientific). Red cell-encapsulated carboxyhemoglobin (HbCO) and oxygenated or deoxygenated Mb were equilibrated to 25 or 37° C. in separate glass vials. Reaction was initiated by injecting Mb into the RBC solution for a final concentration of 40 µM of both proteins. An equivalent volume of PBS (with or without dithionite) was injected into a control sample of carboxylated RBCs. Periodically, 0.5 ml of the reaction and the control sample were taken and centrifuged for 30-60 seconds at 5000×g in 1.5 mL microcentrifuge tubes. The supernatant containing Mb was removed (5 mM sodium dithionite was added in aerobic experiments to prevent autoxidation of the protein) and stored on ice. A solution of 0.5% NP40 in PBS (always containing 5 mM sodium dithionite for anaerobic experiments and sometimes for aerobic) was added to the red cell pellet to lyse the cells. Hb absorbance in the lysed RBC solution was measured with the Cary 50 spectrophotometer in a 1 cm path length cuvette. This cycle was repeated six times, each 1.5-5 minutes, giving six absorbance measurements of the Hb. The control and reaction samples were continuously stirred. The time when absorbance of hemoglobin was measured in the reaction was assumed to be the time elapsed after injection of Mb to 15 or 30 seconds after the start of centrifugation (for 30 or 60 second centrifugation durations, respectively). After the last (6$^{th}$) time point was measured, absorbance of the stored supernatant samples of the reaction and control mixtures was recorded.

In some experiments, the RBCs were not separated from Mb. Instead, absorbance of the whole mixture was recorded with the Integrating Sphere attachment of a Cary 100 spectrophotometer. This setup collects light scattered by the RBCs, thereby providing absorbance spectra sufficiently accurate for spectral deconvolution. The procedure for these experiments was the same as that for mixing Mb with pure HbCO in the Cary 50, after preparation of carboxylated red cells.

Least Squares Deconvolution

Standard reference spectra of the oxidized (met), deoxygenated (deoxy), oxygenated ($O_2$) and carboxylated (CO) forms of hemoglobin (Hb), and myoglobin (Mb) were obtained. After thawing protein on ice, spectra of the oxidized form were obtained by mixing with an excess of potassium ferricyanide and passing through an Econo-Pac 10DG desalting column (Bio-Rad Laboratories, Hercules, Calif.). Spectra of deoxygenated species were recorded after adding an excess of sodium dithionite to the oxidized form. Spectra of the oxygenated form were recorded immediately after passing deoxygenated species through the desalting column under aerobic conditions. Spectra of the carboxylated form were measured after mixing the deoxygenated species with CO-saturated buffer in a ratio of 1:4. All standard spectra were collected at 20° C., 25° C., and 37° C. on the Cary 50 spectrophotometer. Deconvolution of experimental spectra was performed with a least-squares fitting routine in Microsoft Excel. Because the change in absorbance of the kinetic experiments is relatively small, all spectra composed of both Hb and Mb were always fit between 450 and 700 nm, 490 and 650 nm, and 510 and 600 nm, with and without constraining the Hb and Mb concentrations to be equal to each other, in order to confirm the accuracy of the deconvolution. For the same purpose, in some instances, a parameter that could shift the spectra horizontally, along the wavelength axis, was also included in the fit. Absorbance spectra from anaerobic experiments were deconvoluted using carboxylated and deoxygenated standards of Hb and Mb. Absorbance spectra from aerobic experiments were deconvoluted using the standards of the oxidized, carboxylated and oxygenated forms of Hb and Mb. For the RBC experiments where Hb was separated from Mb and dithionite was afterwards added to either RBCs in aerobic experiments or to the supernatant in anaerobic experiments, deoxygenated standards were used in deconvolution instead of the oxygenated and oxidized forms. Before deconvoluting spectra collected with the stopped-flow spectrometer, and sometimes those with the HP8453, absorbance values were remapped to the same wavelengths as those used by the Cary 50 spectrophotometer using the interp1 function of Matlab, employing piecewise cubic hermite interpolation.

Reduction of Oxygen Carriers

In order to make the oxygen carriers readily bind CO, they must be in the $Fe^{2+}$ form (reduced form) and not in the oxidized $Fe^{3+}$ form. The oxidized form will not interact with CO and be ineffective. To achieve the reduced state of oxygen carrier, a strong reducing agent was added and then removed prior to administration. To keep the protein in a reduced form, ascorbic acid and/or N-acetylcysteine, milder reducing agents that are safe and regularly administered in humans, can be added.

FIG. 2 provides a flow diagram for the oxygen carrier preparation process. The first step is to reduce the agent with a strong reductant, such as sodium dithionite (a common industrial reductant). Dithionite itself has an $LD_{50}$ of 2500 mg/kg body weight in rats. To minimize the amount administered, the sodium dithionite salt was removed through a G25 separation column. The preparation has about a 90% removal rate (GE). This was prepared with anaerobic buffer (PBS) in anaerobic conditions under a hood.

After this step, the agent was reduced in the deoxy-state. Then a small concentration of reducing agent was added to maintain the agent in this reduced state. The agents that were used are safe for human application in small quantities, such as 1.25 mM dithionite in mice. The predicted human $LD_{50}$ is 0.5 g/kg, and the mice weigh approximately 25 g so the $LD_{50}$ dose in mice is about 62.5 mg; the present studies used 0.067 mg total. Dithionite is found in 0.10% in the formulation of oxymorphone hydrochloride IV (NUMORPHAN™), which equates to about 100 mg per 100 mL of solution. Other agents that work for this process, for example, are ascorbic acid, N-acetylcysteine, methylene blue, glutathione and cytochrome b5/b5-reductase. Ascorbic acid and N-acetylcysteine are used for therapeutic purposes in humans and extremely well tolerated. The maximal daily doses are 6 g IV for ascorbic acid and 300 mg/kg (or 25 g) for N-acetylcysteine. Methylene blue recommended dosing for treatment of methemoglobinemia is 1 to 2 mg/kg or 50 $mg/m^2$ repeated twice IV.

The agent was then sealed and stored at −80° C. Upon thawing, the agent remained in a >95% reduced form. FIG. 3 shows a flow diagram for the preparation and administration of oxygen carriers as CO scavenging agents.

Example 3: In Vitro Model of CO Poisoning

Figure 4A:
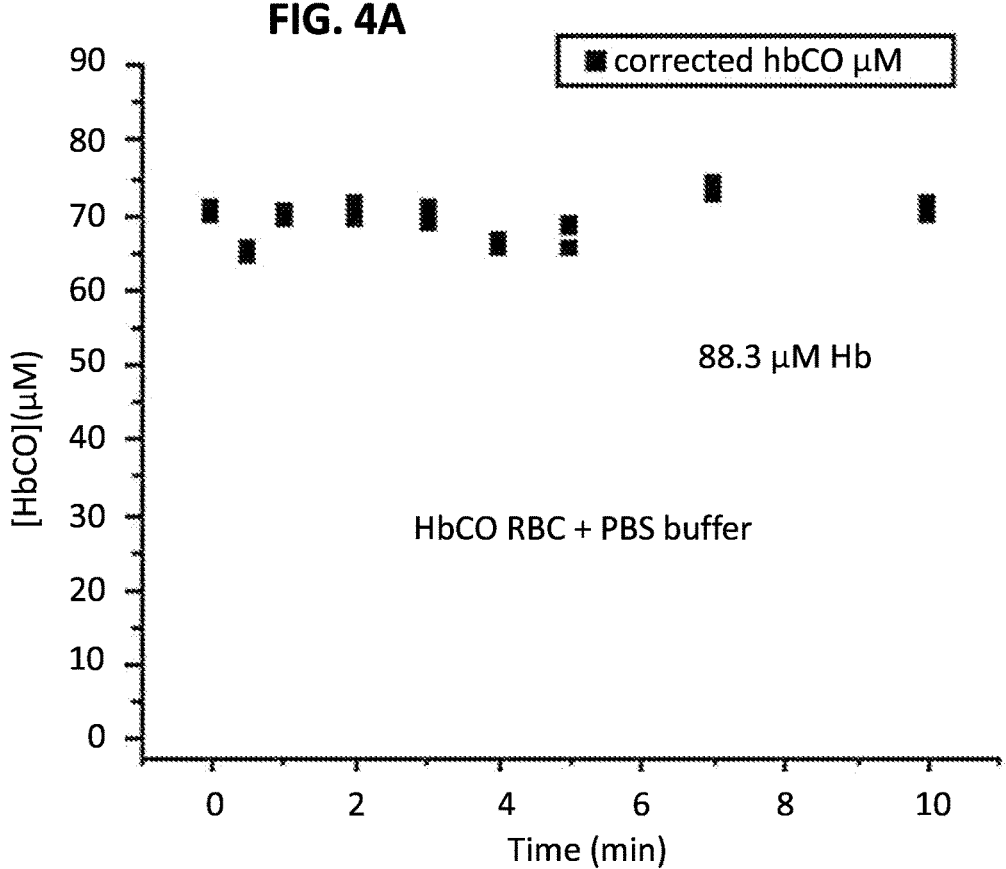
FIGS. 4A-4C are graphs showing the in vitro binding of CO from hemoglobin by wild type equine myoglobin. PBS or myoglobin (100 µL) was infused into a solution containing carboxylated red blood cells in the presence of 5 mM sodium dithionite at 37° C. Samples were taken from the reaction mixture at several time points and the RBCs were separated from the supernatant (containing the Mb) by centrifugation. The amount of HbCO/MbCO in each fraction was determined by UV-vis spectroscopy.
Figure 4B:
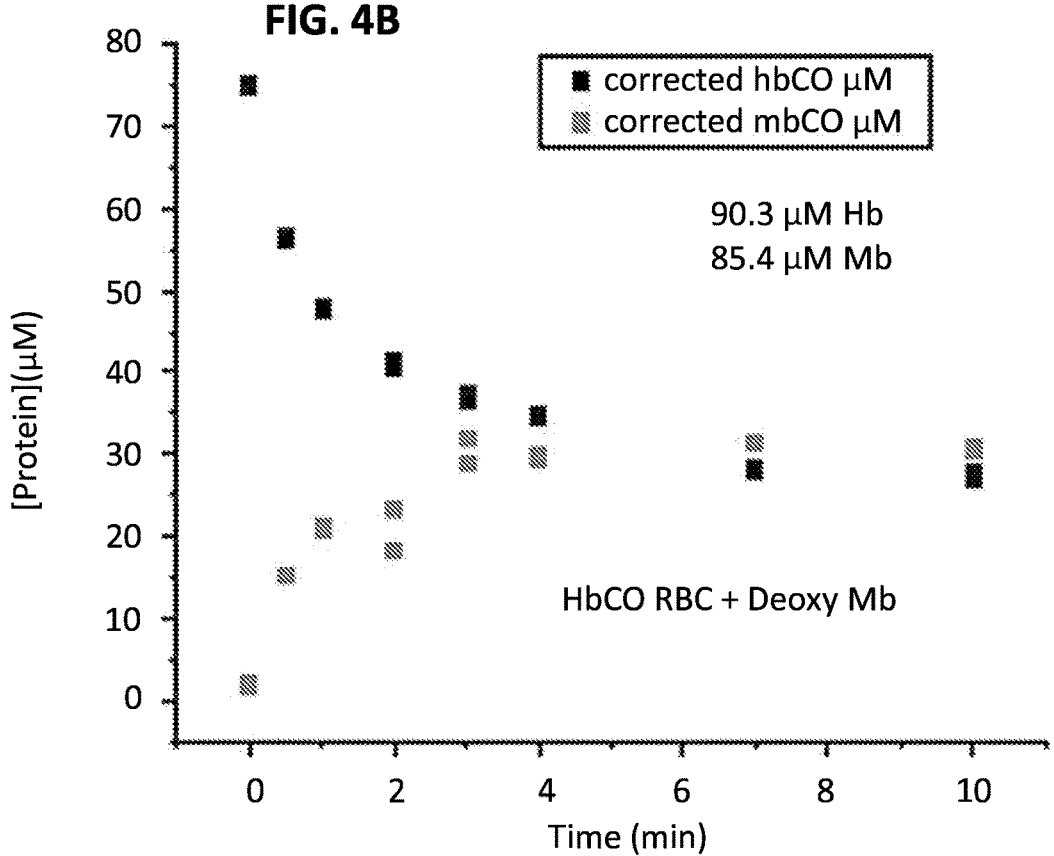
Figure 4C:
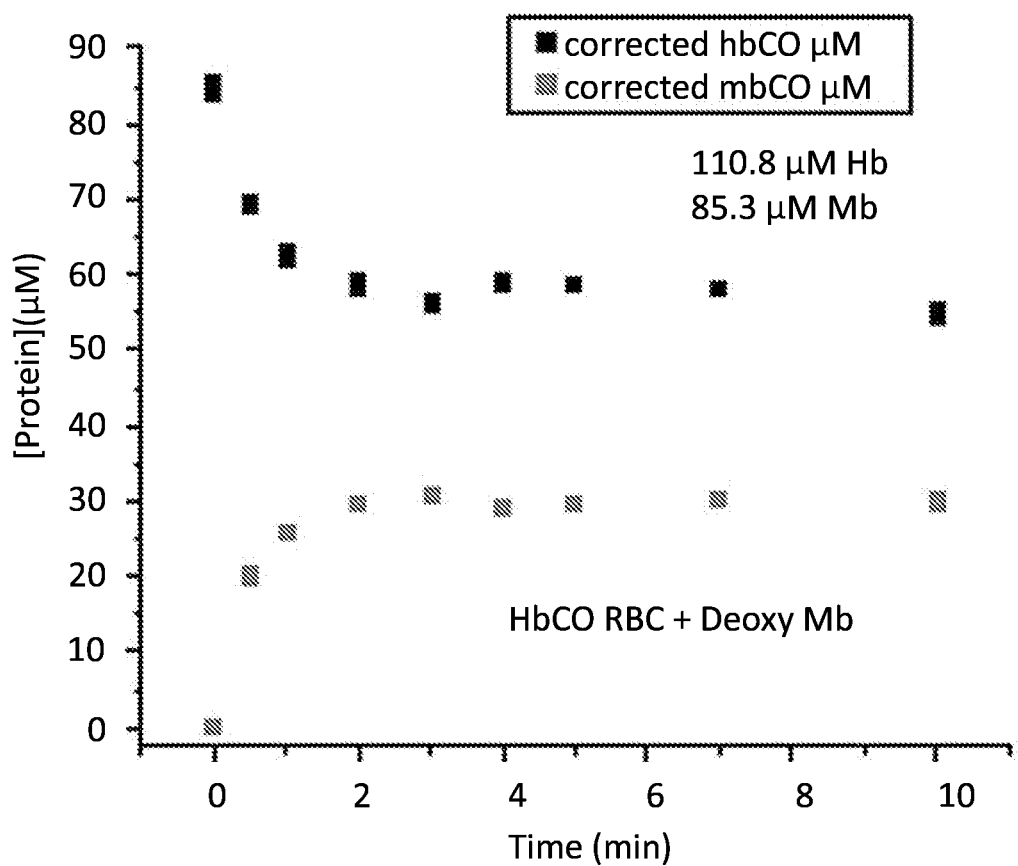

Oxygen carriers will scavenge CO away from the HbCO complex in CO poisoning. In an in vitro model of this scavenging process, 100% HbCO was put into solution in anaerobic conditions. When PBS was added, the concentration of HbCO, as measured by spectroscopy, did not change. When 100% deoxy-myoglobin was added to this solution in a 1:1 ratio, more than half of the HbCO was reduced and the CO bound by myoglobin. When added in deficit to the HbCO (110.8 µM HbCO versus 85.3 µM deoxy-myoglobin), the HbCO concentration was reduced by one third (FIG. 4).

Example 4: Oxygen Carriers Reverse Hemodynamic Collapse and Improve Survival in a Severe CO Poisoning Mouse Model Models of CO poisoning were established in rodents. Using these models, it was demonstrated that myoglobin and hemoglobin act as antidotal agents that can: 1) scavenge CO from in vivo hemoglobin, 2) reverse hemodynamic collapse induced by CO poisoning and 3) reverse mitochondrial respiration inhibition caused from CO toxicity.

Figure 5:
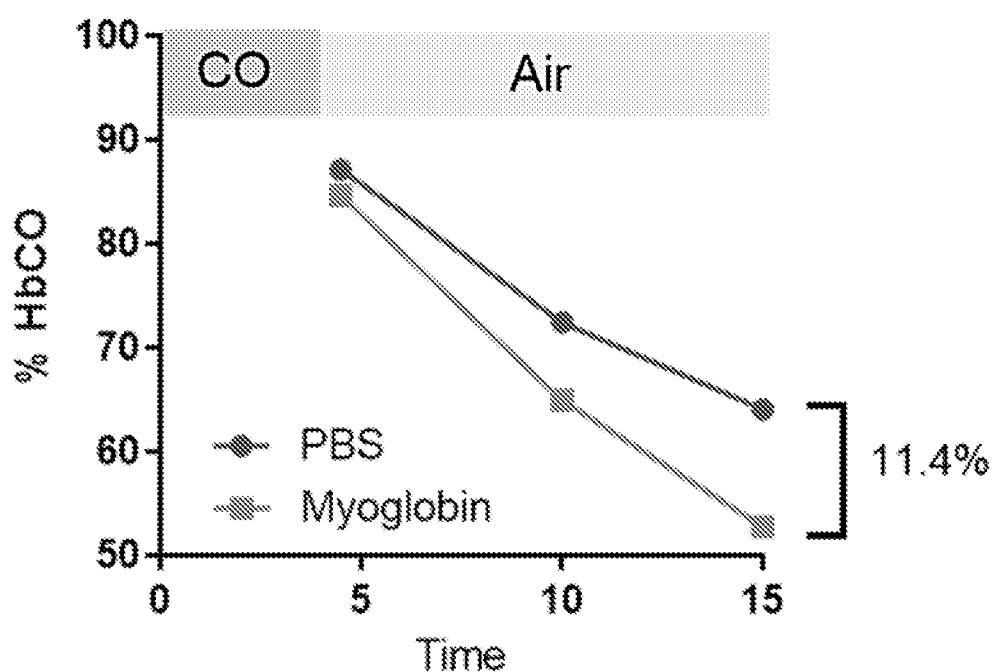
FIG. 5 is a graph showing the in vivo binding of CO from hemoglobin by wild type equine myoglobin in a mouse model for severe CO poisoning.

To establish a model for cardiovascular and mortality end points, tracheally intubated, ventilated, anesthetized mice were exposed to 30,000 ppm (3%) CO gas, with 21% oxygen and 1.5% isoflurane for 4.5 minutes. Mice were surgically instrumented with placement of jugular venous (for infusion of drug) and carotid arterial (for blood pressure and heart rate monitoring) catheters. In this model, there was 88.2% (15/17) mortality in a group infused with 300 µL of PBS post exposure, while all mice that received an infusion of 11 mM myoglobin survived (0% mortality; n=5). Survival of mice infused with myoglobin was due to the reversal in hemodynamic collapse and bradycardia induced by CO (FIG. 5).

Figure 6:
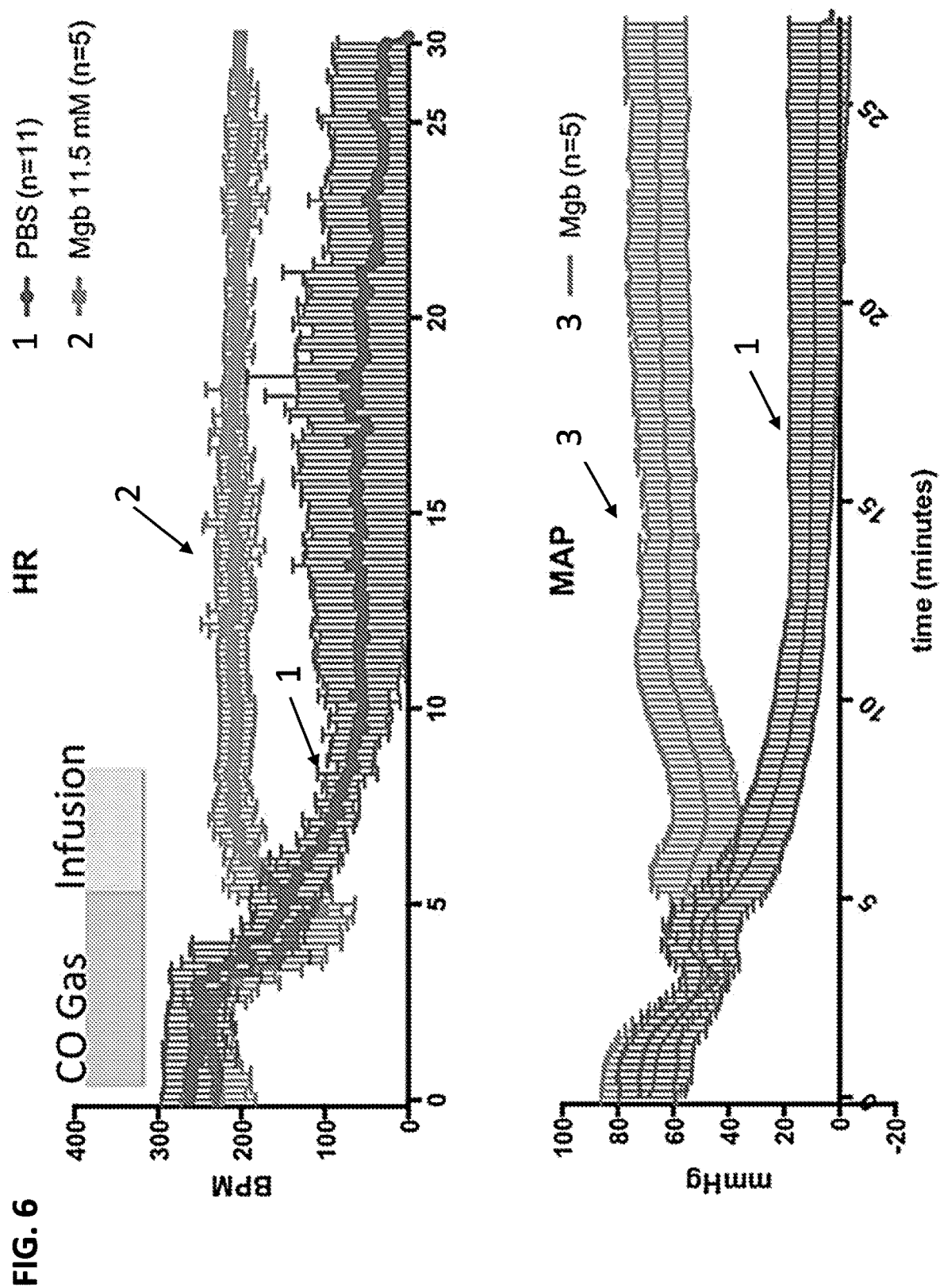
FIG. 6 is a pair of graphs showing the effect of severe CO poisoning on heart rate (HR; top) and mean arterial blood pressure (MAP; bottom), which is reversed with the addition of myoglobin.

Through the jugular venous catheter, the HbCO level was sampled using spectrometry. Immediately after 4.5 minutes of CO exposure, the HbCO level was on average 84 to 88%. Five minutes after infusion of PBS or equine myoglobin, the HbCO level had been reduced to 72.5% and 65.04% respectively. Ten minutes after treatment, the HbCO levels were further reduced to 64.2% and 52.8% respectively. Mouse half-life for CO is much faster than for humans. It was demonstrated that the infusion of myoglobin significantly reduced the level of HbCO faster than fluid and stopping exposure. As shown in FIG. 6, after 4.5 minutes of 3% CO gas exposure to ventilated mice, infusion of 300 μL of PBS resulted in a mortality rate of 88.2% (deaths recorded in blue). The infusion of 300 μL of 11.5 mM reduced myoglobin resulted in 0% mortality (red). Survival in mice infused with reduced myoglobin resulted from a restoration of heart rate (top) and mean arterial blood pressure (bottom).

Figure 7:
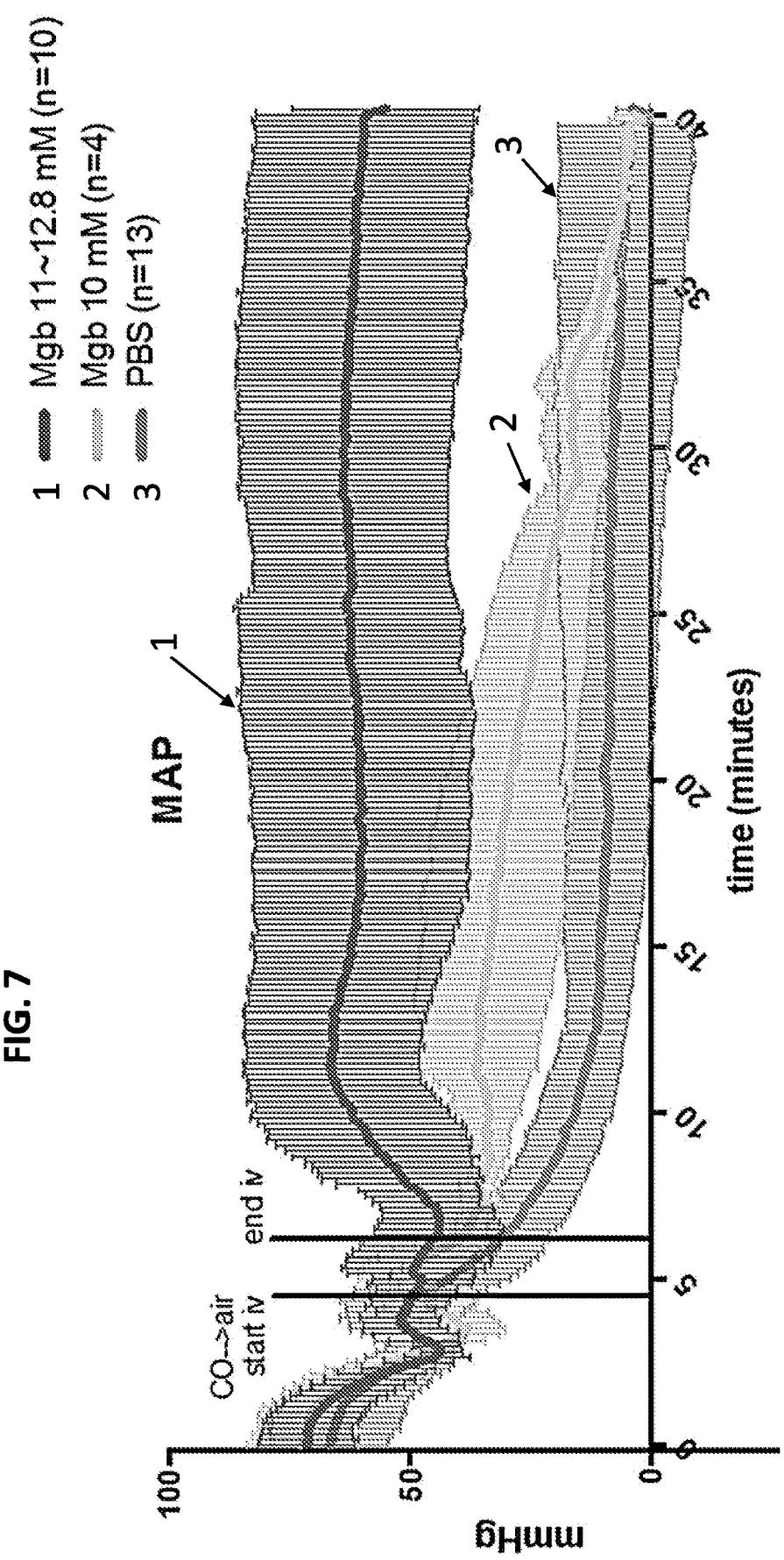
FIG. 7 is a graph showing the effect of severe CO poisoning on blood pressure and heart rate, which is reversed with the addition of myoglobin. Two different doses of myoglobin are shown.

Concentrations of myoglobin less than 11 mM did not confer the same survival benefit (0% survival, n=4), compared to PBS (7.69%, n=13) and myoglobin concentration greater than 11 mM (100% survival, n=10) (FIG. 7). As shown in FIG. 7, greater than 11 mM of myoglobin was needed to reverse the hemodynamic collapse induced by severe CO poisoning. This is due to the stoichiometric binding of CO from HbCO complexes by the reduced oxygen carrier. In similar manner, met- (or oxidized) forms of oxygen carriers do not participate in this scavenging and thus are ineffective. Therefore, it is necessary to prepare reduced oxygen carriers in order to make this therapy effective.

Figure 8:
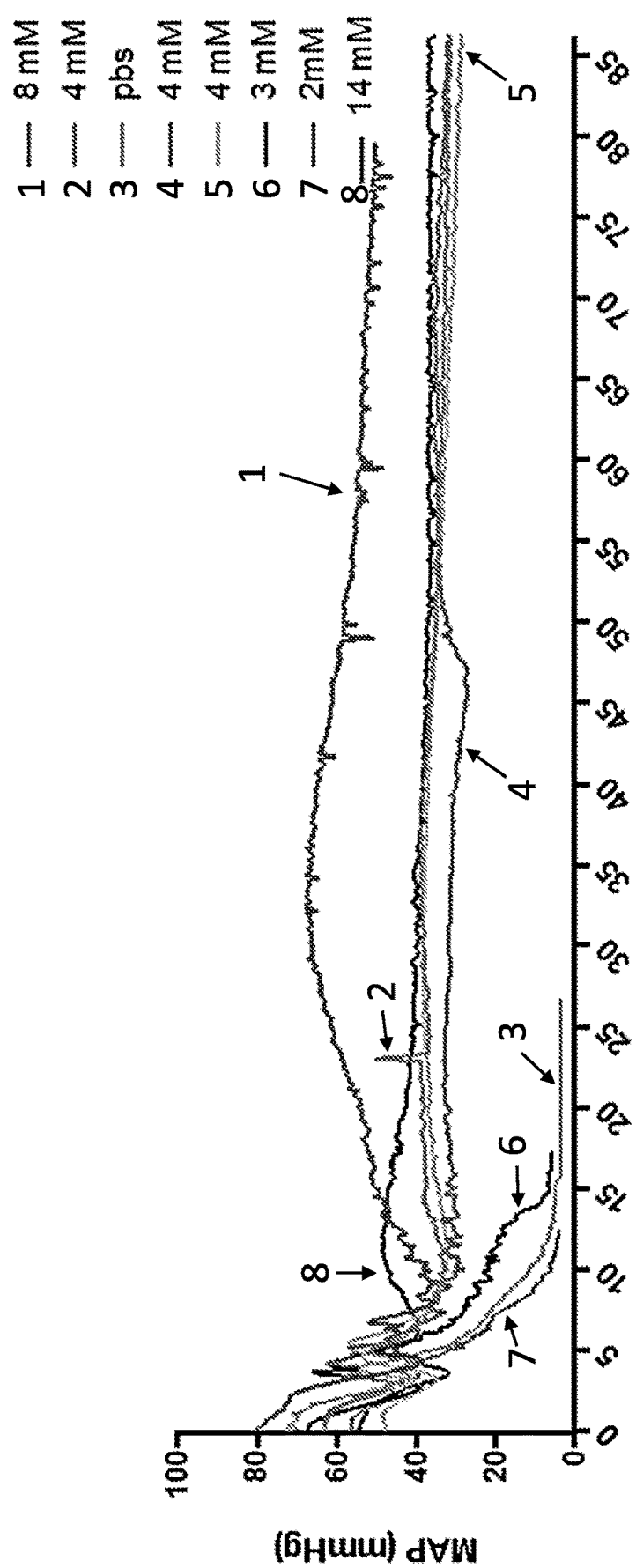
FIG. 8 is a graph showing the effect of severe CO poisoning on blood pressure and heart rate, which is reversed with the addition of hemoglobin. Multiple different doses of hemoglobin are shown.

Similar to myoglobin, hemoglobin was infused to mice in the severe CO poisoning model. This also showed the remarkable ability to reverse the hemodynamic collapse induced by severe CO poisoning (FIG. 8). As shown in FIG. 8, hemoglobin infusion reversed the hemodynamic collapse induced by severe CO poisoning. Concentrations less than 4 mM did not reverse these effects due to the nature of the CO scavenging process. Again, as the CO is scavenged from HbCO in a stoichiometric fashion, the concentration of hemoglobin was quite concentration dependent. The concentration required to reverse hemodynamic collapse was at an inflection point at ≥mM—mice infused with <4 mM died, while those infused with ≥4 mM all survived.

Example 5: Measuring the Safety of Oxygen Carriers in Healthy Mice

Hemoglobin and myoglobin infusion in healthy mice was well tolerated. Healthy mice were anesthetized with 3% isoflurane gas and myoglobin and hemoglobin were injected into the retro-orbital space. The mice were observed for 48 hours. The mice exhibited slightly reduced activity after anesthesia and weight loss in the ensuing 24 hours, however, they resumed normal activity and gained weight thereafter. At 48 hours, the animals were sacrificed, their serum was analyzed for blood chemistries and whole blood was tested for complete blood count. The hematology profile revealed only a slight decline in platelets, which was also present amongst control animals. Blood chemistries showed normal kidney and liver function. This suggests that myoglobin and hemoglobin, even when injected in high quantities (8-12 mM) is safe and well tolerated in mice.

Example 6: Measuring the Ability of CO Scavenging Agents to Reverse CO Induced Mitochondrial Inhibition Mitochondrial respiration was measured before and after CO gas exposure in a Clark-type oxygen electrode respirometry system. The effects of infusion of both reduced hemoglobin and myoglobin were evaluated. Fresh liver was collected from a normal rat, and mitochondria were isolated through differential centrifugation. For left ventricle (LV) tissue, fresh LV was collected from a normal rat and then homogenized. The resulting mitochondria and LV tissue was put into the Clark-type electrode air tight reaction chamber, then substrates (succinate (mitochondria) or malate and pyruvate (LV) and ADP) were added. Mitochondria respired to 0% oxygen and then the system was reoxygenated with a pipetted injection of room air. Mitochondria respired back down to the desired $O_2$ concentration. At this point, CO was added, either in gas form or saturated PBS solution. The system was then reoxygenated, and respiration occurred down to 0%. These rates of respiration were compared with pre-CO exposure. The reason for the first reoxygenation step was to more equally compare rates of mitochondria that have experienced some hypoxia, which can damage their function. After this was completed, CO scavenging agents were added, the system was reoxygenated and this final rate of respiration was compared both to pre-CO and post-CO respiration.

Figure 9:
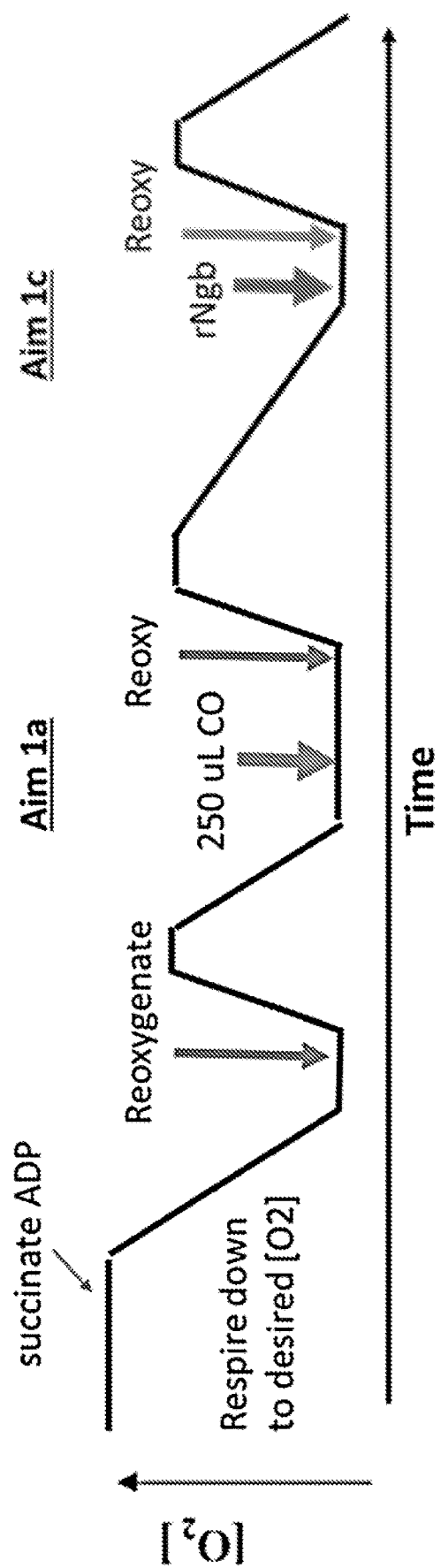
FIG. 9 is a flow diagram of the setup for mitochondrial respiration studies disclosed herein.

As shown in FIG. 9, after addition of ADP/succinate, mitochondria respired to the desired $O_2$ concentration, the system was reoxygenated, and mitochondria respired to the desired level $O_2$ again. CO was then infused, the system was reoxygenated, and rates of respiration were compared. After respiration to 0% $O_2$, myoglobin was infused, the system was reoxygenated and the rates were compared.

Figure 10A:
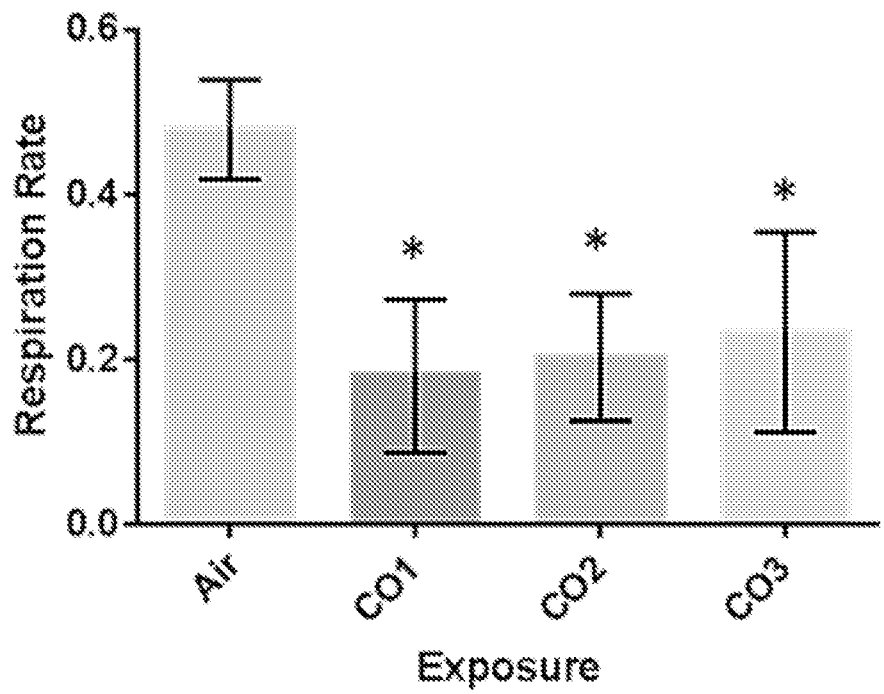
FIGS. 10A-10B are a pair of graphs showing the effect of CO on mitochondrial and cardiac tissue respiration.
Figure 10B:
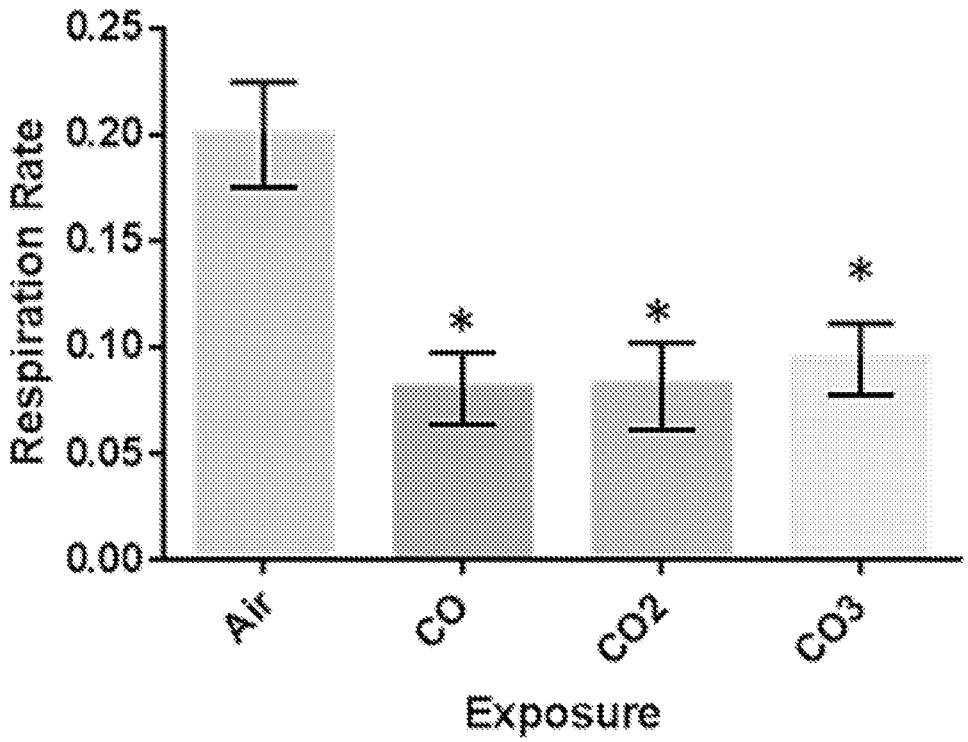

Example 7: The Ability of Hemoglobin and Myoglobin to Reverse Mitochondrial CO Toxicity CO poisoning has long term effects on patients, and one theory is the poisoning of mitochondria leads to generation of increased reactive oxygen species (ROS) through the inhibition of complex IV of the electron transport chain. A model to measure the amount of inhibition produced by CO exposure and quantify it through respiratory rates was developed. In a Clark electrode, the oxygen respiration of isolated mitochondria from rat livers and left ventricle (LV) homogenate was measured, with the addition of the substrates succinate and ADP to measure maximal respiration. It was demonstrated that CO gas induced a persistent decrease in mitochondrial respiration in isolated mitochondria (FIG. 10A) and LV heart tissue (FIG. 10B) over 3 reoxygenations (infusing oxygen back into the respirometry system and letting the mitochondria respire again to 0% oxygen). This effect was stronger in more hypoxic states, consistent with the known competition between CO and $O_2$ for binding at the heme in cytochrome c oxidase (62% reduction in hypoxia versus ~50% in normoxia). This demonstrated the ability to measure mitochondrial function in CO poisoning under normoxia and hypoxia for further testing of binding and inhibitory concentrations of CO at different oxygen tensions in isolated mitochondria and heart tissue.

Example 8: The Ability of Reduced Hemoglobin and Reduced Myoglobin to Reverse the Effects of CO Toxicity in Tissue Respiration A further study demonstrated that deoxy-Hb reversed the effects of CO poisoning on mitochondria. CO gas induced a decrease of 60.5% from maximal respiration ($p=2.3\times10^{-7}$). The addition of deoxy-Hb in a 0.5 equimolar solution increased the poisoned respiration rate by 95% ($p=0.0003$, unpaired t-test) (FIG. 11).

Another study demonstrated that deoxy-myoglobin increased respiration of LV homogenate following exposure to CO. As shown in FIG. 12, CO gas induced a decrease of 75.6% from maximal respiration ($p=0.0004$). The addition of 0.5 equimolar deoxy-myoglobin increased the respiration rate by 199% (p=0.0096, unpaired t-test). There was no recovery in respiration without treatment after CO exposure.

Example 9: Artificial Oxygen Carriers Reverse Hemodynamic Collapse and Improve Survival in a Severe CO Poisoning Mouse Model Models of CO poisoning were established in rodents, as described in Example 4. Using these models, it was demonstrated that an artificial oxygen carrier, PEGylated hemoglobin (PEG-Hb; surface conjugation of polyethylene glycol to human hemoglobin), acts as antidotal agent that can: 1) scavenge CO from in vivo hemoglobin, and 2) reverse hemodynamic collapse induced by CO poisoning. PEG-Hb has been tested in humans as a hemoglobin-based oxygen carrier (Björkholm et al., *Haematologica* 90 (4):505-515, 2005; Olofsson et al., *Anesthesiology* 105(6):1153-1163, 2006; Olofsson et al., *Transfus Med* 18(1):28-39, 2008), but has not been studied in models of CO poisoning.

Tracheally intubated, ventilated, anesthetized mice were exposed to 30,000 ppm (3%) CO gas, with 21% oxygen and 1.5% isoflurane for 4.5 minutes. Mice were surgically instrumented with placement of jugular venous (for infusion of drug) and carotid arterial (for blood pressure and heart rate monitoring) catheters. In this model, all mice that received PEG-Hb (n=3) survived. The concentration infused was 10 mM at approximately 200 to 250 microliters volume.

Figure 13:
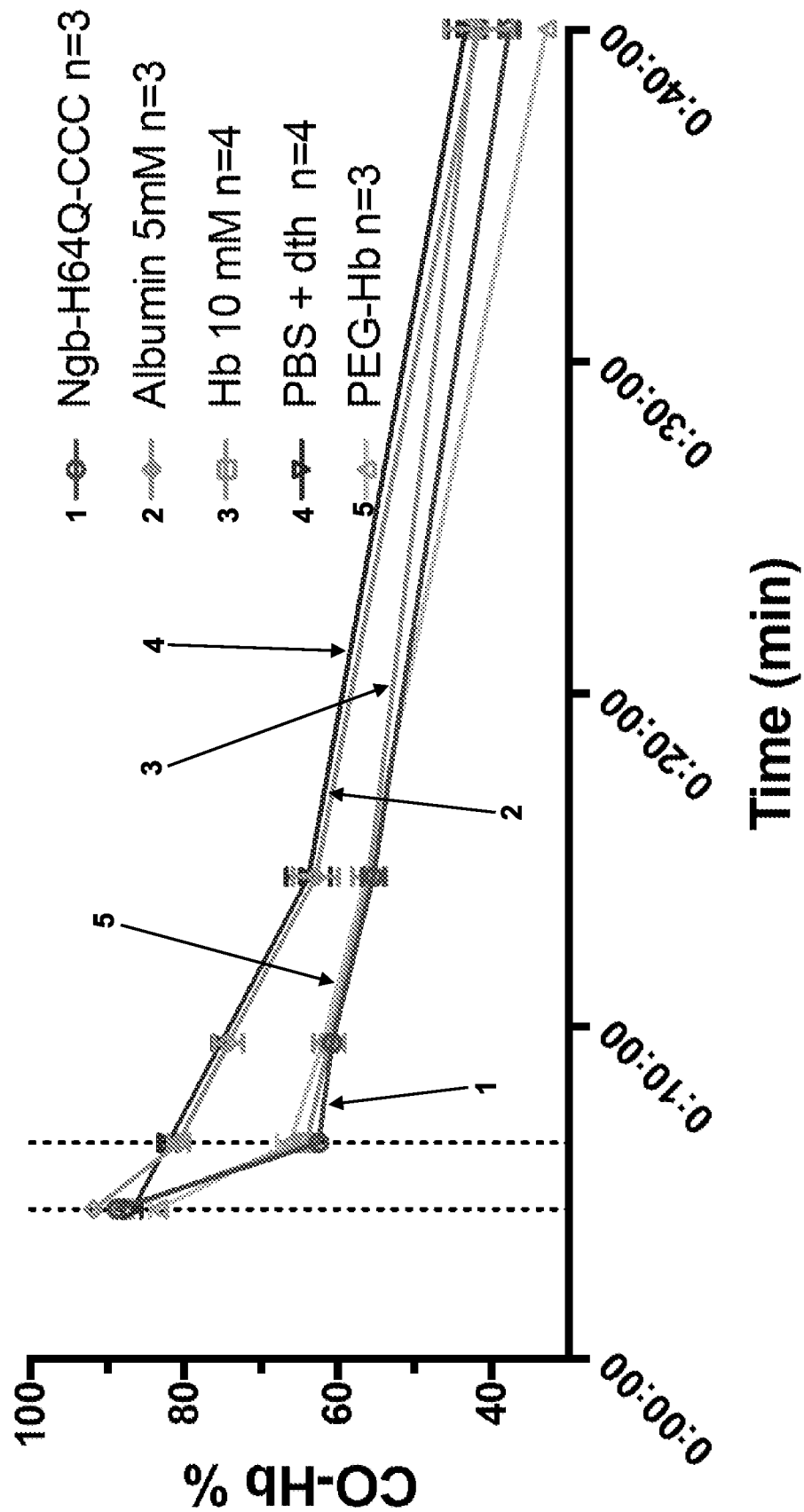
FIG. 13 is a graph showing a time course of HbCO levels in mice exposed to 30,000 ppm (3%) CO gas and subsequently treated with PEGylated hemoglobin (PEG-Hb).
Figure 14:
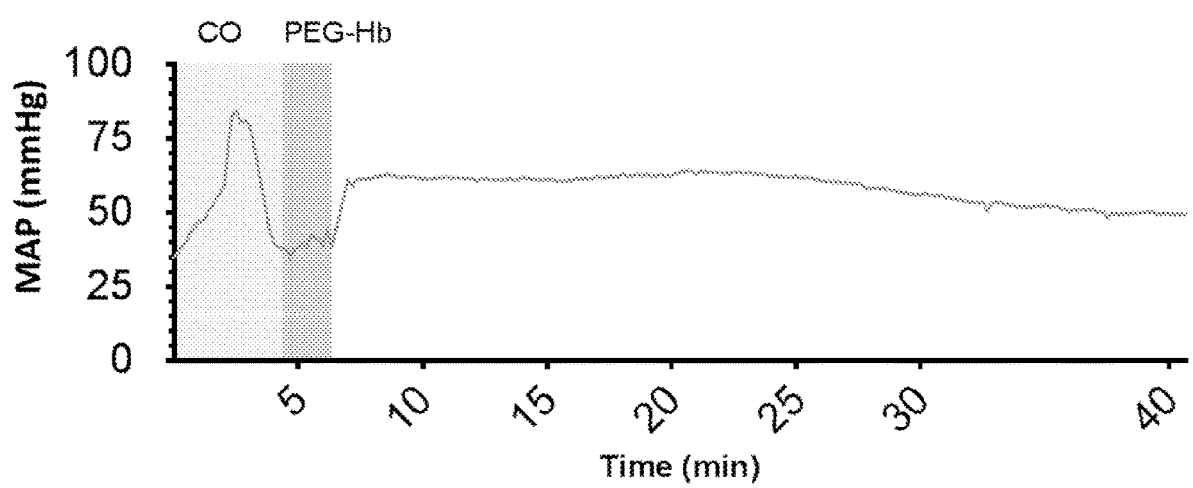
FIG. 14 is a graph showing mean arterial pressure (MAP) over time of mice exposed to 30,000 ppm (3%) CO gas and subsequently treated with PEG-Hb.

Through the jugular venous catheter, the HbCO level was sampled using spectrometry. Immediately after 4.5 minutes of CO exposure, the HbCO level was on average 84 to 88%. As shown in FIG. 13, five minutes after infusion of PBS, albumin or PEG-Hb, the HbCO levels were reduced to 82%, 80% and 66%, respectively. Ten minutes after treatment, the HbCO levels were further reduced to 76%, 75% and 62%, respectively. Mouse half-life for CO is much faster than for humans. These results demonstrate that infusion of PEG-Hb significantly reduced the level of HbCO faster than fluid and stopping exposure. As shown in FIG. 14, after 4.5 minutes of 3% CO gas exposure to ventilated mice, infusion of 200-250 µL of 10 mM reduced PEG-Hb restored mean arterial blood pressure (MAP). All mice administered PEG-Hb survived due to the restoration in MAP.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of treating carboxyhemoglobinemia in a subject, comprising:
    selecting a subject with carboxyhemoglobinemia, wherein the subject has at least 5% carboxyhemoglobin in their blood;
    administering to the subject a therapeutically effective amount of a composition comprising a natural oxygen carrier, wherein the oxygen carrier is in the reduced form, and wherein the oxygen carrier is hemoglobin; and
    wherein the therapeutically effective amount of the composition is an amount sufficient to scavenge carbon monoxide in the blood or tissues of the subject, thereby reducing the level of carboxyhemoglobin in the blood of the subject.

2. The method of claim 1, wherein the composition further comprises a pharmaceutically acceptable reducing agent.

3. The method of claim 2, wherein the reducing agent comprises sodium dithionite, ascorbic acid, N-acetylcysteine, methylene blue, glutathione, cytochrome b5/b5-reductase, hydralazine or any combination thereof.

4. The method of claim 1, wherein the hemoglobin is human hemoglobin.

5. The method of claim 1, wherein the hemoglobin is non-human animal hemoglobin.

6. A method of scavenging carbon monoxide from hemoglobin in blood or tissue of a subject, wherein the subject has at least 5% carboxyhemoglobin in their blood, comprising contacting the blood or tissue with a composition comprising a natural oxygen carrier, wherein the oxygen carrier is in the reduced form, and wherein the oxygen carrier is hemoglobin;
    thereby scavenging carbon monoxide from hemoglobin in the blood or tissue.

7. The method of claim 6, wherein contacting the blood or tissue with a composition comprising a natural oxygen carrier comprises administering a therapeutically effective amount of the composition comprising the natural oxygen carrier, wherein the oxygen carrier is in the reduced form, and wherein the oxygen carrier is hemoglobin to the subject;
    wherein the therapeutically effective amount is an amount sufficient to scavenge carbon monoxide in the blood or tissue of the subject, thereby reducing the level of carboxyhemoglobin in the blood of the subject.

8. The method of claim 7, comprising selecting a subject with carboxyhemoglobinemia prior to administering the composition to the subject.

9. The method of claim 7, wherein the subject has at least 10% carboxyhemoglobin in their blood.

10. The method of claim 6, wherein the composition further comprises a reducing agent.

11. The method of claim 10, wherein the reducing agent comprises sodium dithionite, ascorbic acid, N-acetylcysteine, methylene blue, glutathione, cytochrome b5/b5-reductase, hydralazine, or any combination thereof.

12. The method of claim 6, wherein the hemoglobin is human hemoglobin.

13. The method of claim 6, wherein the hemoglobin is non-human animal hemoglobin.

* * * * *